(12) United States Patent
Barlaam

(10) Patent No.: US 8,318,752 B2
(45) Date of Patent: Nov. 27, 2012

(54) 4-(3-CHLORO-2-FLUOROANILINO)-7-METHOXY-6-{[1-(N-METHYLCARBAMOYL-METHYL)PIPERIDIN-4-YL]OXY} QUINAZOLINE, ITS PHARMACEUTICALLY ACCEPTABLE SALTS, AND PHARMACEUTICAL COMPOSITIONS COMPRISING THE SAME

(75) Inventor: Bernard Barlaam, Södertälje (SE)

(73) Assignee: Astrazeneca AB, Sodertalje (SE)

( * ) Notice: Subject to any disclaimer, the term of this patent is extended or adjusted under 35 U.S.C. 154(b) by 115 days.

(21) Appl. No.: 10/571,991

(22) PCT Filed: Sep. 15, 2004

(86) PCT No.: PCT/GB2004/003937
§ 371 (c)(1),
(2), (4) Date: Mar. 15, 2006

(87) PCT Pub. No.: WO2005/028469
PCT Pub. Date: Mar. 31, 2005

(65) Prior Publication Data
US 2008/0096881 A1    Apr. 24, 2008

(30) Foreign Application Priority Data

Sep. 19, 2003  (EP) .................................... 03292309
May 14, 2004  (EP) .................................... 04291248

(51) Int. Cl.
*A61K 31/517*    (2006.01)
(52) U.S. Cl. ...................... 514/266.4; 544/326; 546/242
(58) Field of Classification Search ............... 514/266.4; 544/326; 546/242
See application file for complete search history.

(56) References Cited

U.S. PATENT DOCUMENTS

| | | | |
|---|---|---|---|
| 3,985,749 A | 10/1976 | Foster | |
| 4,332,420 A | 6/1982 | Coski | |
| 4,335,127 A | 6/1982 | Vandenberk et al. | |
| 4,640,920 A | 2/1987 | Boyle et al. | |
| 4,921,863 A | 5/1990 | Sugimoto et al. | |
| 5,252,586 A | 10/1993 | Cain et al. | |
| 5,405,843 A | 4/1995 | Fukazawa et al. | |
| 5,457,105 A | 10/1995 | Barker | |
| 5,576,322 A | 11/1996 | Takase et al. | |
| 5,616,582 A | 4/1997 | Barker | |
| 5,721,237 A | 2/1998 | Myers et al. | |
| 5,747,498 A | 5/1998 | Schnur et al. | |
| 5,770,599 A | 6/1998 | Gibson | |
| 5,770,603 A | 6/1998 | Gibson | |
| 5,821,246 A | 10/1998 | Brown et al. | |
| 5,866,572 A | 2/1999 | Barker et al. | |
| 5,929,080 A | 7/1999 | Frost et al. | |
| 5,962,458 A | 10/1999 | Lohmann et al. | |
| 6,004,967 A | 12/1999 | McMahon et al. | |
| 6,046,206 A | 4/2000 | Pamukcu et al. | |
| 6,117,433 A | 9/2000 | Edens et al. | |
| 6,126,917 A | 10/2000 | Mishani et al. | |
| 6,177,433 B1 | 1/2001 | Uckun et al. | |
| 6,225,318 B1 | 5/2001 | Sobolov-Jaynes et al. | |
| 6,297,258 B1 | 10/2001 | Wissner et al. | |
| 6,313,130 B1 | 11/2001 | Uckun et al. | |
| 6,326,373 B1 | 12/2001 | Uckun et al. | |
| 6,384,223 B1 | 5/2002 | Gletsos | |
| 6,562,319 B2 | 5/2003 | Mishani et al. | |
| 6,627,651 B1 | 9/2003 | Shirishi et al. | |
| 6,653,305 B2 | 11/2003 | Himmelsbach et al. | |
| 6,740,651 B2 | 5/2004 | Himmelsbach et al. | |
| 6,924,285 B2 * | 8/2005 | Himmelsbach et al. | ... 514/234.8 |
| 6,972,288 B1 | 12/2005 | Himmelsbach et al. | |
| 7,119,084 B2 | 10/2006 | Himmelsbach et al. | |
| 7,148,230 B2 | 12/2006 | Bradbury et al. | |
| 7,160,981 B2 | 1/2007 | La Thangue et al. | |
| 7,294,629 B2 | 11/2007 | Kitano et al. | |
| 2002/0049197 A1 | 4/2002 | Himmelsbach et al. | |
| 2002/0082270 A1 | 6/2002 | Himmelsbach et al. | |
| 2002/0082271 A1 | 6/2002 | Himmelsbach et al. | |

(Continued)

FOREIGN PATENT DOCUMENTS

CA    2086968 A1    7/1993

(Continued)

OTHER PUBLICATIONS

Patani, et al. in Chem. Rev., 96, 1996, pp. 3147-3176.*
Harris et al., poster presented at the XXII European Colloquium on Heterocyclic Chemistry (XXII ECHC-2006) in Bari, Italy, on Sep. 2-6, 2006.
Office Action in copending U.S. Appl. No. 10/572,048 mailed Oct. 31, 2008.
Office action in Australian application No. 2004274227, the Australian counterpart to the present application, dated Jun. 27, 2007.
English translation of the opposition writ in Chilean application 2355/2004, the Chilean counterpart to the present application dated Jul. 27, 2006.

(Continued)

*Primary Examiner* — Douglas M Willis
(74) *Attorney, Agent, or Firm* — Astrazeneca AB

(57) ABSTRACT

The invention concerns quinazoline derivatives of Formula (I): wherein each of $R^1$, $X^1$, $R^2$, $R^3$, $R^5$, n and m have any of the meanings defined in the description; processes for their preparation, pharmaceutical compositions containing them and their use in the manufacture of a medicament for use as an antiproliferative agent in the prevention or treatment of tumors which are sensitive to inhibition of EGF and erbB receptor tyrosine kinases.

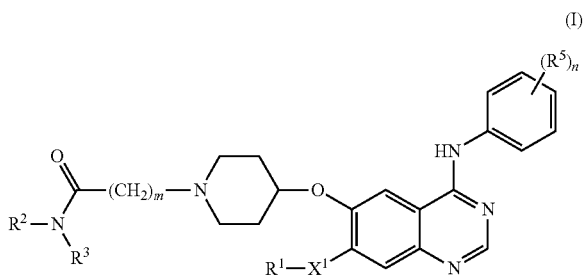

6 Claims, No Drawings

U.S. PATENT DOCUMENTS

| | | |
|---|---|---|
| 2002/0128553 A1 | 9/2002 | Mishani et al. |
| 2002/0169180 A1 | 11/2002 | Himmelsbach et al. |
| 2002/0173509 A1 | 11/2002 | Himmelsbach et al. |
| 2002/0173646 A1 | 11/2002 | Thomas et al. |
| 2002/0177601 A1 | 11/2002 | Himmelsbach et al. |
| 2003/0149062 A1 | 8/2003 | Jung et al. |
| 2003/0158196 A1 | 8/2003 | Jung et al. |
| 2004/0044014 A1 | 3/2004 | Himmelsbach et al. |
| 2004/0048880 A1 | 3/2004 | Himmelsbach et al. |
| 2004/0053972 A1 | 3/2004 | Nara et al. |
| 2004/0176361 A1 | 9/2004 | Fujio et al. |
| 2004/0192664 A1 | 9/2004 | Kunz et al. |
| 2004/0198997 A1 | 10/2004 | Scholz et al. |
| 2005/0130995 A1 | 6/2005 | Nishino et al. |
| 2005/0148607 A1 | 7/2005 | Suzuki et al. |
| 2005/0165035 A1 | 7/2005 | Bradbury |
| 2005/0182043 A1 | 8/2005 | Himmelsbach et al. |
| 2005/0215574 A1 | 9/2005 | Bradbury et al. |
| 2006/0167026 A1 | 7/2006 | Nawa et al. |
| 2006/0188501 A1 | 8/2006 | Homma et al. |
| 2006/0270672 A1 | 11/2006 | Himmelsbach et al. |
| 2007/0037837 A1 | 2/2007 | Hennequin et al. |
| 2007/0043010 A1 | 2/2007 | Bradbury et al. |
| 2007/0099943 A1 | 5/2007 | Bradbury et al. |
| 2008/0096881 A1 | 4/2008 | Hennequin et al. |
| 2009/0312313 A1 | 12/2009 | Shimizu et al. |

FOREIGN PATENT DOCUMENTS

| | | |
|---|---|---|
| CA | 2 375 259 A1 | 12/2000 |
| CA | 2 417 042 A1 | 3/2002 |
| CA | 2 417 050 A1 | 3/2002 |
| CA | 2 417 652 A1 | 1/2003 |
| CA | 2 417 897 A1 | 1/2003 |
| CA | 2 417 907 A1 | 1/2003 |
| EP | 0 288 563 | 11/1988 |
| EP | 0 326 330 | 8/1989 |
| EP | 0 566 226 A | 10/1993 |
| EP | 0 607 439 | 7/1994 |
| EP | 0 602 851 | 10/1996 |
| EP | 0 520 722 | 12/1996 |
| EP | 0 787 722 | 8/1997 |
| EP | 0 837 063 | 4/1998 |
| EP | 0 635 507 | 9/1999 |
| EP | 1 230 919 | 8/2002 |
| EP | 1 283 039 | 2/2003 |
| EP | 1 369 418 | 12/2003 |
| GB | 2033894 | 5/1980 |
| GB | 2160201 | 12/1985 |
| GB | 2295387 | 5/1996 |
| JP | 11-189586 | 7/1999 |
| JP | 2003246780 A | 9/2003 |
| WO | WO 88/02365 | 4/1988 |
| WO | WO 92/14746 | 9/1992 |
| WO | WO 92/20642 | 11/1992 |
| WO | WO 93/08170 | 4/1993 |
| WO | WO 93/17682 | 9/1993 |
| WO | WO 94/27965 | 12/1994 |
| WO | WO 95/00146 | 1/1995 |
| WO | WO 95/03283 | 2/1995 |
| WO | WO 95/15758 | 6/1995 |
| WO | WO 95/24190 | 9/1995 |
| WO | WO 96/09294 | 3/1996 |
| WO | WO 96/15118 | 5/1996 |
| WO | WO 96/16960 | 6/1996 |
| WO | WO 96/30347 | 10/1996 |
| WO | WO 96/33977 | 10/1996 |
| WO | WO 96/33978 | 10/1996 |
| WO | WO 96/33979 | 10/1996 |
| WO | WO 96/33980 | 10/1996 |
| WO | WO 96/33981 | 10/1996 |
| WO | WO 96/39145 | 12/1996 |
| WO | WO 97/03069 | 1/1997 |
| WO | WO 97/11692 | 4/1997 |
| WO | WO 97/18813 | 5/1997 |
| WO | WO 97/22596 | 6/1997 |
| WO | WO 97/30034 | 8/1997 |
| WO | WO 97/30035 | 8/1997 |
| WO | WO 97/30044 | 8/1997 |
| WO | WO 97/32856 | 9/1997 |
| WO | WO 97/38983 | 10/1997 |
| WO | WO 97/38994 | 10/1997 |
| WO | WO 97/42187 | 11/1997 |
| WO | WO 98/02434 | 1/1998 |
| WO | WO 98/13354 | 4/1998 |
| WO | WO 98/38984 | 9/1998 |
| WO | WO 98/50038 | 11/1998 |
| WO | WO 98/50370 | 11/1998 |
| WO | WO 99/06378 | 2/1999 |
| WO | WO 99/09016 | 2/1999 |
| WO | WO 99/10349 | 3/1999 |
| WO | WO 99/24037 | 5/1999 |
| WO | WO 99/35132 | 7/1999 |
| WO | WO 99/61428 | 12/1999 |
| WO | WO 00/00202 | 1/2000 |
| WO | WO 00/06555 | 2/2000 |
| WO | WO 00/09481 | 2/2000 |
| WO | WO 00/10981 | 3/2000 |
| WO | WO 00/12497 | 3/2000 |
| WO | WO 00/18740 | 4/2000 |
| WO | WO 00/20402 | 4/2000 |
| WO | WO 00/24718 | 5/2000 |
| WO | WO 00/44728 | 8/2000 |
| WO | WO 00/47212 | 8/2000 |
| WO | WO 00/51587 | 9/2000 |
| WO | WO 00/51991 | 9/2000 |
| WO | WO 00/55141 | 9/2000 |
| WO | WO 00/55162 | 9/2000 |
| WO | WO 00/56338 | 9/2000 |
| WO | WO 00/56720 | 9/2000 |
| WO | WO 00/68203 | 11/2000 |
| WO | 00/72849 A1 | 12/2000 |
| WO | WO 00/73260 | 12/2000 |
| WO | WO 00/78735 | 12/2000 |
| WO | WO 01/04102 | 1/2001 |
| WO | WO 01/07432 | 2/2001 |
| WO | WO 01/12227 | 2/2001 |
| WO | 01/19788 A2 | 3/2001 |
| WO | 01/21160 A2 | 3/2001 |
| WO | WO 01/21594 | 3/2001 |
| WO | WO 01/21595 | 3/2001 |
| WO | WO 01/21596 | 3/2001 |
| WO | WO 01/21597 | 3/2001 |
| WO | 01/32155 A2 | 5/2001 |
| WO | WO 01/32632 | 5/2001 |
| WO | WO 01/32651 | 5/2001 |
| WO | WO 01/45641 | 6/2001 |
| WO | 01/64642 A2 | 9/2001 |
| WO | WO 01/66099 | 9/2001 |
| WO | WO 01/76586 | 10/2001 |
| WO | WO 01/77085 | 10/2001 |
| WO | WO 01/94341 | 12/2001 |
| WO | WO 01/98277 | 12/2001 |
| WO | 02/05791 A2 | 1/2002 |
| WO | WO 02/16352 | 2/2002 |
| WO | 02/17712 A2 | 3/2002 |
| WO | 02/20020 A1 | 3/2002 |
| WO | WO 02/18351 | 3/2002 |
| WO | WO 02/18370 | 3/2002 |
| WO | WO 02/18372 | 3/2002 |
| WO | WO 02/18373 | 3/2002 |
| WO | WO 02/18376 | 3/2002 |
| WO | WO 02/24684 | 3/2002 |
| WO | 02/30358 A2 | 4/2002 |
| WO | WO 02/30924 | 4/2002 |
| WO | WO 02/34711 | 5/2002 |
| WO | WO 02/34744 | 5/2002 |
| WO | WO 02/41882 A | 5/2002 |
| WO | WO 02/44166 | 6/2002 |
| WO | WO 02/48117 | 6/2002 |
| WO | WO 02/50043 | 6/2002 |
| WO | WO 02/056882 | 7/2002 |
| WO | WO 02/062767 | 8/2002 |
| WO | WO 02/066445 | 8/2002 |
| WO | WO 02/068409 | 9/2002 |
| WO | WO 02/073235 | 9/2002 |
| WO | WO 02/076976 | 10/2002 |

| | | |
|---|---|---|
| WO | WO 02/092577 | 11/2002 |
| WO | WO 02/092578 | 11/2002 |
| WO | WO 02/092579 | 11/2002 |
| WO | WO 02/094760 | 11/2002 |
| WO | WO 03/000188 | 1/2003 |
| WO | WO 03/082831 * | 3/2003 |
| WO | 03/031406 A2 | 4/2003 |
| WO | WO 03/040108 | 5/2003 |
| WO | WO 03/040109 | 5/2003 |
| WO | WO 03/045364 | 6/2003 |
| WO | WO 03/045395 | 6/2003 |
| WO | WO 03/049740 | 6/2003 |
| WO | WO 03/064413 | 8/2003 |
| WO | WO 03/082290 A | 10/2003 |
| WO | WO 03/082831 A | 10/2003 |
| WO | 03/097086 A2 | 11/2003 |
| WO | 03/097615 A1 | 11/2003 |
| WO | 03/099276 A1 | 12/2003 |
| WO | 2004006846 A2 | 1/2004 |
| WO | 2004/010929 A2 | 2/2004 |
| WO | 2004013091 A2 | 2/2004 |
| WO | 2004/072038 A1 | 8/2004 |
| WO | WO 2004/064718 | 8/2004 |
| WO | 2004/085385 A2 | 10/2004 |
| WO | 2004/096224 A2 | 11/2004 |
| WO | WO 2004/093880 | 11/2004 |
| WO | WO 2004/096226 | 11/2004 |
| WO | 2005/001053 A2 | 1/2005 |
| WO | 2005/003325 A2 | 1/2005 |
| WO | 2005/016347 A1 | 2/2005 |
| WO | WO 2005/012290 | 2/2005 |
| WO | WO 2005/026150 | 3/2005 |
| WO | WO 2005/026151 | 3/2005 |
| WO | WO 2005/026152 | 3/2005 |
| WO | WO 2005/026156 | 3/2005 |
| WO | WO 2005/026157 | 3/2005 |
| WO | WO 2005/028469 | 3/2005 |
| WO | WO 2005/028470 | 3/2005 |
| WO | 2005/030140 A2 | 4/2005 |
| WO | WO 2005/030757 | 4/2005 |
| WO | WO 2005/030765 | 4/2005 |
| WO | WO 2005/041973 | 5/2005 |
| WO | WO 2005/051923 | 6/2005 |
| WO | WO 2005/075439 | 8/2005 |
| WO | WO 2005/118572 | 12/2005 |
| WO | WO 2006/064196 | 6/2006 |
| WO | WO 2006/090163 | 8/2006 |
| WO | WO 2006/092573 | 9/2006 |
| WO | WO 2006/092574 | 9/2006 |
| WO | WO 2006/117521 | 11/2006 |
| WO | WO 2006/117523 | 11/2006 |
| WO | WO 2007/034143 | 3/2007 |
| WO | WO 2007/034144 | 3/2007 |
| WO | WO 2007/063291 | 6/2007 |
| WO | WO 2007/063293 | 6/2007 |
| WO | 2008076415 A1 | 6/2008 |

OTHER PUBLICATIONS

European file history in European Patent 1667992, the European counterpart to the present application.
Office action in Singapore application 200601647-1, the Singapore counterpart to the present application dated Sep. 7, 2007.
Corrected version of Examination report in Singapore application 200601647-1, the Singapore counterpart to the present application dated Sep. 5, 2008.
Hennequin, L.F., et al."Novel 4-Anilinoquinazolines With C-7 Basic Side Chains: Design and Structure Activity Relationship of a Series of Potent, Orally Active VEGF Receptor Tyrosine Kinase Inhibitors", Journal of Medical Chemistry, American Chemical Society, vol. 45, pp. 1300-1312.
In re Hilmer, 359 F.2d 859,149 USPQ 480 (CCPA 1966).
In re Deckler, 977 F.2d 1449, 24 USPQ2d 1448 (Fed. Cir. 1992).
Ex parte Tytgat, 225 USPQ 907 (Bd. Pat. App. &Inter. 1985).
37 CFR §41.127(a)(1).
Ex parte Kimura, 55 USPQ2d 1537 (Bd. Pat. App. & Inter. 2000).
Ex parte A, 17 USPQ2d 1716 (Bd. Pat. App. & Inter. 1990).
Net Money/N, Inc. v. Verisign, Inc., 545 F.3d 1359 (Fed. Clr. 2008).
*Eisai Co. Ltd.* v. *Teva Pharmaceuticals USA, Inc.*, 533 F.3d 1353 (Fed. Cir. 2008).
In re Baird, 16 F.3d 380, 382, 29 USPQ2d 1550 (Fed. Cir. 1994).
In re Jones, 958 F.2d 347 (Fed. Cir. 1992).
*Takeda Chemical Industries, Ltd.* v. *Alphapharm Pty., Ltd.*, 492 F.3d 1350 (Fed. Cir. 2007).
In re Deuel, 51 F.3d 1552 (Fed. Cir. 1995).
Pages from Federal Register's Notice of Proposed Rulemaking, 49 FR 3768, dated Jan. 30, 1984.
*Tafas* v. *Doll*, slip op. (Fed. Cir. Mar. 20, 2009).
In re Wilding, 535 F.2d 631 (1976, CCPA).
In re Kaplan, 789 F.2d 1574 (Fed. Cir. 1986).
In re Sarrett, 327 F.2d 1005, (CGPA 1964).
*The Procter & Gamble Company* v. *Teva Pharmaceuticals USA, Inc.*, _F.3d_, No. 2008-1404, -1405, -1406 (Fed. Cir. May 13, 2009).
In re Kubin, _F.3d _, No. 2008-1184, (Fed. Cir. Apr. 3, 2009).
Hickinson et al. "AZD8931, an Equipotent, Reversible Inhibitor of Signaling by Epidermal Growth Factor Receptor, ERBB2 (HER2) and ERBB3: A Unique Agent for Simultaneous ERBB Receptor Blockade in Cancer". Clin. Cancer Res. (2010), vol. 16, No. 4, 1159-1169.
Keilholz et al. "Phase I Dose-Finding Study of Monotherapy with AZD8931, an Inhibitor of erbB1, 2 and 3 Signaling, in Patients with Advanced Solid Tumors". J Clin Oncol. (2011), vol. 29, Abstract 3097.
Keilholz et al. "Phase I Dose-Finding Study of Monotherapy with AZD8931, an Inhibitor of erbB1, 2 and 3 Signaling, in Patients with Advanced Solid Tumors". ASCO (2011), Poster.
Klinowska et al. "AZD8931, an Equipotent, Reversible Inhibitor of erbB1, erbB2 and erbB3 Receptor Signaling: Characterisation of Pharmacological Profile". European Journal of Cancer Supplements (2009), vol. 7, No. 2, 127.
Lopez-Martin et al. "Phase I Dose-Finding Study of AZD8931, an Inhibitor of erbB1, 2 and 3 Receptor Signaling, in Combination with Paclitaxel". J Clin. Oncol. (2011), vol. 29, Abstract 3105.
Lopez-Martin et al. "Phase I Dose-Finding Study of AZD8931, an Inhibitor of erbB1, 2 and 3 Receptor Signaling, in Combination with Paclitaxel". ASCO (2011), Poster.
Marshall et al. "Evaluation of AZD8931, an Equipotent Inhibitor of erbB1, erbB2 and erbB3 Receptor Signaling, on Ligand Stimulated Breast Cancer Cell Lines with Differing Levels of erbB2 Expression". SABC (2009), Abstract 5059.
Normanno et al. "Target-based therapies in breast cancer: current status and future perspectives". Endocr Relat Cancer (2009), vol. 16(3): 675-702.
Speake et al. "Characterization of AZD8931, a Potent Reversible Small Molecule Inhibitor Against Epidermal Growth Factor Receptor (EGFR), Erythroblastic Leukemia Viral Oncogene Homolog 2 (HER2) and 3 (HER3) with a Unique and Balanced Pharmacological Profile". J Clin. Oncol. (2009), vol. 27, 15s, Abstract 11072.
United States Court of Appeals for the Federal Circuit, *Genetics Institute, LLC* v. *Novartis Vaccines and Diagnostics, Inc.*, 2010-124; Appeal from the USDC for the District of Delaware in Case No. 08-CV-0290, Judge Sue L. Robinson, Decided Aug. 23, 2011.
Ballard, Peter et al, "5-Substituted 4-anilinoquinazolines as potent, selective and orally active inhibitors of erbB2 receptor tyrosine kinase," *Bioorganic & Medicinal Chemistry Letters* 15(19):4226-4229 (2005).
Hennequin, Laurent et al, "Novel 4-anilinoquinazolines with C-6 carbon-linked side chains: Synthesis and structure-activity relationship of a series of potent, orally active, EGF receptor tyrosine kinase inhibitors," *Bioorganic & Medicinal Chemistry Letters* 16(10):2672-2676 (2006).
Ballard, Peter et al, "Inhibitors of epidermal growth factor receptor tyrosine kinase: Novel C-5 substituted anilinoquinazolines designed to target the ribose pocket," *Bioorganic & Medicinal Chemistry Letters* 16(6):1633-1637 (2006).
Ballard, Peter et al, "Inhibitors of epidermal growth factor receptor tyrosine kinase: Optimization of potency and in vivo pharmacokinetics," *Bioorganic & Medicinal Chemistry Letters* 16(18):4908-4912 (2006).

Harris, Craig et al, "Selective alkylation of a 6,7-dihydroxyquinazoline," *Tetrahedron Letters* 46(45):7715-7719 (2005).
Harris, Craig et al, "Facile synthesis of 7-amino anilinoquinazolines via direct amination of the quinazoline core," *Tetrahedron Letters* 46(43):7381-7384 (2005).
Ballard, P. et al., "Inhibitors of epidermal growth factor receptor tyrosine kinase: Optimisation of potency and in vivo pharmacokinetics," Bioorg. Med. Chem. lett. 16:4908-4912 (2006).
Barker et al., Studies Leading to the Identification of ZD1839 (Iressa™): An Orally Active, Selective Epidermal Growth Factor Receptor Tyrosine Kinase Inhibitor Targeted to the Treatment of Cancer, Bioorg. Med. Chem. Lett. 11(14): 1911-1914 (2001).
Bridges et al., "Tyrosine kinase inhibitors. 8. An unusually steep structure-activity relationship for analogues of 4-(3-bromoanilino)-6,7-dimethoxyquinazoline (PD 153035), a potent inhibitor of the epidermal growth factor receptor," J. Med. Chem. 39: 267-276 (1996).
Chevalier et al., "Induction of DNA replication by peroxisome proliferators is independent of both tumour necrosis factor (alpha) priming and EGF-receptor tyrosine kinase activity," J. Cell Sci. 112(24): 4785-4791 (1999).
Denny et al., "Structure-Activity Relationships for 4-Anilinoquinazolines as Potent Inhibitors at the ATP Binding Site for the Epidermal Growth Factor Receptor in vitro," Clinical and Experimental Pharmacology and Physiology 23:424-427 (1996).
Gazit et al., "Tyrophostins IV-Highly Potent Inhibitors . . . Relationship Study of 4-Anilidoquinazolines," Bioorganic & Medicinal Chemistry 48(8): 1203-1207 (1996).
Ghosh et al., "Structure-based design of potent inhibitors of EGF-receptor tyrosine kinease as anti-cancer agents," Anti-Cancer Drug Design 14, 403-410 (1999).
Hennequin et al., "Design and structure-activity relationship of a new class of potent VEGF receptor tyrosine kinase inhibitors," J. Med. Chem. 42: 5369-5389 (1999).
March, J., Advanced Organic Chemistry—Reactions, Mechanisms, and Structure, 4$^{th}$ Ed., © 1992, John Wiley & Sons, New York, NY, p. 357.
Mendelsohn et al., "Status of Epidermal Growth Factor Receptor Antagonists in the Biology and Treatment of Cancer," J. Clinical Oncology 21(14): 2787-2799 (2003).
Mendelsohn, "Targeting the Epidermal Growth Factor Receptor for Cancer Therapy," Journal of Clinical Oncology 20(18s):2s-13s (2002).
Myers et al., "The preparation and SAR of 4-(anilion), 4-(phenoxy), and 4-(thiophenoxy)-quinzolines: inhibitors of p56lck and EGF-R tyrosine kinase activity," Biorg. Med. Chem. Lett. 7(4): 417-420 (1997).
Pao et al., "Epidermal Growth Factor Receptor Mutations, Small-Molecule Kinase Inhibitors, and Non-Small-Cell Lung Cancer: Current Knowledge and Future Directions," Journal of Clinical Oncology 23(11):1-13 (2005).
Rewcastle et al., "Tyrosine Kinase Inhibitors. 5 . . . 4-(Phenylamino)quinazolines as Potent . . . Inhibitors of the Tyrosine Kinase Domain of the Epidermal Growth Factor Receptor," J. Med. Chem. 38:3482-3487 (1995).
Singh et al., "Inhibitors of the epidermal growth factor receptor protein tyrosine kinase: A quantitative structure-activity relationship analysis," J. Enzyme Inhibition 13:125-134 (1998).
Smaill et al., "Tyrosine kinase inhibitors. 17. Irreversible inhibitors of the epidermal growth factor receptor: 4-(Phenylamino)quinazoline- and 4-(Phe-nylamino)pyrido," J. Med. Chem. 43(16):3199 (2000).
Stamos et al., "Structure of the Epidermal Growth Factor Receptor Kinase Domain Alone and in Complex with a 4-Anilinoquinazoline Inhibitor," J. Bio. Chem. 277(48):46265-46272 (2002).
Traxler, "Oncologic, Endocrine & Metabolic: Protein tyrosine kinase inhibitors in cancer treatment," Expert Opinion on Therapeutic Patents 7:571-588 (1997).
Traxler, "Monthly Focus: Oncologic, Endocrine & Metabolic: Tyrosine kinase inhibitors in cancer treatment (Part II)," Expert Opinion on Therapeutic Patents 8:1599-1625 (1998).
Tsou et al., "6-Substituted-4-(3-bromophenylamino)quinazolines As Putative Irreversible Inhibitors of the Epidermal Growth Factor Receptor (Egfr) and Human Epidermal Growth Factor Receptor (Her-2) Tyrosine Kinases with Enhanced Antitumor Activity," J. Med. Chem. 44:2719-2734 (2001).
Vema et al., "Design of EGFR Kinase Inhibitors: A Ligand-Based Approach and its Confirmation with Structure-Based Studies," Bioorg. Med. Chem. 11:4643-4653 (2003).
Wright et al., "Allosteric inhibition of fructose-1,6-bisphosphatase by anilinoquinazolines," Bioorg. Med. Chem. Lett. 11(1):17-21 (2001).
Decision in Patent Interferences 105,595 McK and 105,596 McK dated Jun. 17, 2008.
English Translation of Office Action in Japanese Patent Appln. No. 2003-580299, the Japanese counterpart of the present application, dated May 11, 2006.
Response to Office Action in Japanese Patent Appln. No. 2003-580299, the Japanese counterpart of the present application, dated Jul. 28, 2006.
English translation of Response to Office Action in Japanese Patent Appln. No. 2003-580299, the Japanese counterpart of the present application, dated Jul. 28, 2006.
English translation of Response to Office Action in Japanese Patent Appln. No. 2003-580299, the Japanese counterpart of U.S. Appl. No. 10/508,675, dated Oct. 26, 2006.
Office Action in Indian Patent Appln. No. 2630/DELNP/2004, the Indian counterpart of the present application, dated Apr. 20, 2006.
Response to Office Action in Indian Patent Appln. No. 2630/DELNP/2004, the Indian counterpart of the present application, dated Jul. 24, 2006.
English translation of Office Action in Chinese Patent Appln. No. 03811739.8, the Chinese counterpart of the present application, dated Jul. 21, 2006.
Response to Office Action in Chinese Patent Appln. No. 03811739.8, the Chinese counterpart of U.S. Appl. No. 10/508,675, dated Dec. 5, 2006.
English translation of Response to Office Action in Chinese Patent Appln. No. 03811739.8 of U.S. Appl. No. 10/508,675, dated Dec. 5, 2006.
Communication from European Patent Office in EP Appln. No. 03 710 015.3, the European counterpart of the present application, dated Sep. 22, 2006.
Communication from EPO dated Mar. 9, 2006, in EP Appln. No. 03 710 015.3, the European counterpart of U.S. Appl. No. 10/508,675.
Communication from European Patent Office ("EPO") dated May 27, 2005, in EP Appln. No. 03 710 015.3, the European counterpart of U.S. Appl. No. 10/508,675.
Reply to May 27, 2005 Communication from EPO dated Sep. 20, 2005, in EP Appln. No. 03 710 015.3, the European counterpart of U.S. Appl. No. 10/508,675.
Alferez et al. "Inhibiting Signaling by erbB Receptor Tyrosine Kinases with AZD8931, a Potent Reversible small Molecule Inhibitor, Reduces Intestinal Adenoma Formation in the ApcMin/+ Mouse Model". EORTC-NCI-AACR (2010), Abstract 471.
Alferez et al. "Inhibiting Signaling by erbB Receptor Tyrosine Kinases with AZD8931, a Potent Reversible small Molecule Inhibitor, Reduces Intestinal Adenoma Formation in the ApcMin/+ Mouse Model". EORTC-NCI-AACR (2010), Poster.
Blowers "AZD8931". IASLC Annual Targeted Therapies of the Treatment of Lung Cancer Meeting (2011), Santa Monica, CA, PowerPoint Presentation.
Cristofanilli et al. "Exploratory Subset Analysis According to Prior Endocrine Treatment of Two Randomized Phase II Trials Comparing Gefitinib (G) with Placebo (P) in Combination with Tamoxifen (T) or Anastrozole (A) in Hormone Receptor-Positive (HR+) Metastatic Breast Cancer (MBC)". J Clin. Oncol. (2009), vol. 27, 15s, Abstract 1014.
Marshall et al. "Evaluation of AZD8931, an Equipotent Inhibitor of erbB1, erbB2 and erbB3 Receptor Signaling, on Ligand Stimulated Breast Cancer Cell Lines with Differing Levels of erbB2 Expression". SABCS (2009), Abstract 5059.
Grunwald, V. et al, "Developing Inhibitors of the Epidermal Growth Factor Receptor for Cancer Treatment," *J. National Cancer Institute* 95(12):851-867 (2003).

Office Action in copending U.S. Appl. No. 12/147,250 mailed Aug. 17, 2009.
Office Action in copending U.S. Appl. No. 11/636,549 mailed Sep. 29, 2009.
Office Action in copending U.S. Appl. No. 10/572,048 mailed Jan. 5, 2010.
Office Action in copending U.S. Appl. No. 10/572,048 mailed Jun. 9, 2009.
Office Action in copending U.S. Appl. No. 10/573,352 mailed Oct. 28, 2009.
Office Action in copending U.S. Appl. No. 10/573,352 mailed Mar. 5, 2009.
Chen, et al., "Eludicating inhibitory models of the inhibitors of epidermal growth factor receptor by docking and 3D-QSAR," Bioorganic and Medicinal Chemistry, (2004) 12, 2409-2419.
*Daiichi Sankyo Company, Ltd., et al.* v. *Matrix Laboratories, Ltd., et al.*, Appeal from the US District Court for the District of NJ in Case No. 06-CV-03462. 2009-1511, Decided Sep. 9. 2010.
Hickinson, et al., "AZD8931, an Equipotent, Reversible Inhibitor of Signaling by Epidermal Growth Factor Receptor, ERBB2 (HER2), and ERBB3: A Unique Agent for Simultaneous ERBB Receptor Blockade in Cancer," Clinical Cancer Research (2010) 16,1159-1169.
Liu, et al., "Blockage of epidermal growth factor receptor by quinazoline tyrosine kinase inhibitors suppresses growth of human hepatocellular carcinoma," Cancer Letters (2007), 248, 32-40.
Rewcastle, et al., "Tyrosine Kinase Inhibitors. 12. Synthesis and Structure-Activity Relationships for 6-Substituted 4-(Phenylamino)pyrimido[5,4-d]pyrimidines Designed as Inhibitors of the Epidermal Growth Factor Receptor," J. Med. Chem. (1997) 40, 1820-1826.
Thomson, et al., "Tyrosine Kinase Inhibitors. 13. Structure-Activity Relationships for Soluble 7-Substituted 4-[(3-Bromophenyl)amino]pyrido[4,3-d]pyrimidines Designed as Inhibitors of the Tyrosine Kinase Activity of the Epidermal Growth Factor Receptor," J. Med. Chem. (1997) 40, 3915-3925.
Traxler, et al., "4-(Phenylamino) pyrrolopyrimidines: Potent and Selective, ATP Site Directed Inhibitors of the EGF-Receptor Protein Tyrosine Kinase," J. Med. Chem. (1996) 39, 2285-2292.
International Preliminary Report on Patentability in PCT/GB2004/003937.

\* cited by examiner

4-(3-CHLORO-2-FLUOROANILINO)-7-METHOXY-6-{[1-(N-METHYLCARBAMOYL-METHYL)PIPERIDIN-4-YL]OXY} QUINAZOLINE, ITS PHARMACEUTICALLY ACCEPTABLE SALTS, AND PHARMACEUTICAL COMPOSITIONS COMPRISING THE SAME

The invention concerns certain novel quinazoline derivatives, or pharmaceutically acceptable salts thereof, which possess anti-tumour activity and are accordingly useful in methods of treatment of the human or animal body. The invention also concerns processes for the manufacture of said quinazoline derivatives, to pharmaceutical compositions containing them and to their use in therapeutic methods, for example in the manufacture of medicaments for use in the prevention or treatment of solid tumour disease in a warm-blooded animal such as man.

Many of the current treatment regimes for diseases resulting from the abnormal regulation of cellular proliferation such as psoriasis and cancer, utilise compounds that inhibit DNA synthesis and cellular proliferation. To date, compounds used in such treatments are generally toxic to cells however their enhanced effects on rapidly dividing cells such as tumour cells can be beneficial. Alternative approaches to these cytotoxic anti-tumour agents are currently being developed, for example selective inhibitors of cell signalling pathways. These types of inhibitors are likely to have the potential to display an enhanced selectivity of action against tumour cells and so are likely to reduce the probability of the therapy possessing unwanted side effects.

Eukaryotic cells are continually responding to many diverse extracellular signals that enable communication between cells within an organism. These signals regulate a wide variety of physical responses in the cell including proliferation, differentiation, apoptosis and motility. The extracellular signals take the form of a diverse variety of soluble factors including growth factors as well as paracrine and endocrine factors. By binding to specific transmembrane receptors, these ligands integrate the extracellular signal to the intracellular signalling pathways, therefore transducing the signal across the plasma membrane and allowing the individual cell to respond to its extracellular signals. Many of these signal transduction processes utilise the reversible process of the phosphorylation of proteins that are involved in the promotion of these diverse cellular responses. The phosphorylation status of target proteins is regulated by specific kinases and phosphatases that are responsible for the regulation of about one third of all proteins encoded by the mammalian genome. As phosphorylation is such an important regulatory mechanism in the signal transduction process, it is therefore not surprising that aberrations in these intracellular pathways result in abnormal cell growth and differentiation and so promote cellular transformation (reviewed in Cohen et al, *Curr Opin Chem Biol*, 1999, 3, 459-465).

It has been widely shown that a number of these tyrosine kinases are mutated to constitutively active forms and/or when over-expressed result in the transformation of a variety of human cells. These mutated and over-expressed forms of the kinase are present in a large proportion of human tumours (reviewed in Kolibaba et al., Biochimica et Biophysica Acta, 1997, 133, F217-F248). As tyrosine kinases play fundamental roles in the proliferation and differentiation of a variety of tissues, much focus has centred on these enzymes in the development of novel anti-cancer therapies. This family of enzymes is divided into two groups—receptor and non-receptor tyrosine kinases e.g. EGF Receptors and the SRC family respectively. From the results of a large number of studies including the Human Genome Project, about 90 tyrosine kinase have been identified in the human genome, of this 58 are of the receptor type and 32 are of the non-receptor type. These can be compartmentalised in to receptor tyrosine kinase and 10 non-receptor tyrosine kinase sub-families (Robinson et al, *Oncogene*, 2000, 19, 5548-5557).

The receptor tyrosine kinases are of particular importance in the transmission of mitogenic signals that initiate cellular replication. These large glycoproteins, which span the plasma membrane of the cell possess an extracellular binding domain for their specific ligands (such as Epidermal Growth Factor (EGF) for the EGF Receptor). Binding of ligand results in the activation of the receptor's kinase enzymatic activity that is encoded by the intracellular portion of the receptor. This activity phosphorylates key tyrosine amino acids in target proteins, resulting in the transduction of proliferative signals across the plasma membrane of the cell.

It is known that the erbB family of receptor tyrosine kinases, which include EGFR, erbB2, erbB3 and erbB4, are frequently involved in driving the proliferation and survival of tumour cells (reviewed in Olayioye et al., *EMBO J.*, 2000, 19, 3159). One mechanism in which this can be accomplished is by overexpression of the receptor at the protein level, generally as a result of gene amplification. This has been observed in many common human cancers (reviewed in Klapper et al., *Adv. Cancer Res.*, 2000, 77, 25) such as breast cancer (Sainsbury et al., *Brit. J. Cancer*, 1988, 58, 458; Guerin et al., *Oncogene Res.*, 1988, 3, 21; Slamon et al., *Science*, 1989, 244, 707; Klijn et al., *Breast Cancer Res. Treat.*, 1994, 29, 73 and reviewed in Salomon et al., *Crit. Rev. Oncol. Hematol.*, 1995, 19, 183), non-small cell lung cancers (NSCLCs) including adenocarcinomas (Cerny et al., *Brit. J. Cancer*, 1986, 54, 265; Reubi et al., *Int. J. Cancer*, 1990, 45, 269; Rusch et al., *Cancer Research*, 1993, 53, 2379; Brabender et al, *Clin. Cancer Res.*, 2001, 7, 1850) as well as other cancers of the lung (Hendler et al., *Cancer Cells*, 1989, 7, 347; Ohsaki et al., *Oncol, Rep.*, 2000, 7, 603), bladder cancer (Neal et al., *Lancet*, 1985, 366; Chow et al., *Clin. Cancer Res.*, 2001, 7, 1957, Zhau et al., *Mol. Carcinog.*, 3, 254), oesophageal cancer (Mukaida et al., *Cancer*, 1991, 68, 142), gastrointestinal cancer such as colon, rectal or stomach cancer (Bolen et al., *Oncogene Res.*, 1987, 1, 149; Kapitanovic et al., *Gastroenterology*, 2000, 112, 1103; Ross et al., *Cancer Invest.*, 2001, 19, 554), cancer of the prostate (Visakorpi et al., *Histochem. J.*, 1992, 24, 481; Kumar et al., 2000, 32, 73; Scher et al., *J. Natl. Cancer Inst.*, 2000, 92, 1866), leukaemia (Konaka et al., *Cell*, 1984, 37, 1035, Martin-Subero et al., *Cancer Genet Cytogenet.*, 2001, 127, 174), ovarian (Hellstrom et al., *Cancer Res.*, 2001, 61, 2420), head and neck (Shiga et al., *Head Neck*, 2000, 22, 599) or pancreatic cancer (Ovotny et al., *Neoplasma*, 2001, 48, 188). As more human tumour tissues are tested for expression of the erbB family of receptor tyrosine kinases it is expected that their widespread prevalence and importance will be further enhanced in the future.

As a consequence of the mis-regulation of one or more of these receptors, it is widely believed that many tumours become clinically more aggressive and so correlate with a poorer prognosis for the patient (Brabender et al, *Clin. Cancer Res.*, 2001, 7, 1850; Ross et al, *Cancer Investigation*, 2001, 12, 554, Yu et al., *Bioessays*, 2000, 22.7, 673). In addition to these clinical findings, a wealth of pre-clinical information suggests that the erbB family of receptor tyrosine kinases are involved in cellular transformation. This includes the observations that many tumour cell lines overexpress one or more of the erbB receptors and that EGFR or erbB2 when transfected into non-tumour cells have the ability to transform these cells. This tumourigenic potential has been further verified as transgenic mice that overexpress erbB2 spontaneously develop tumours in the mammary gland. In addition to this, a number of pre-clinical studies have demonstrated that anti-proliferative effects can be induced by knocking out one or more erbB activities by small molecule inhibitors, dominant negatives or inhibitory antibodies (reviewed in Mendelsohn et al., *Oncogene*, 2000, 19, 6550). Thus it has been recognised that inhibitors of these receptor tyrosine kinases should be of value as a selective inhibitor of the proliferation of mammalian cancer cells (Yaish et al. *Science*, 1988, 242, 933, Kolibaba et al, Biochimica et Biophysica Acta, 1997, 133, F217-F248; Al-Obeidi et al, 2000, *Oncogene*, 19, 5690-5701; Mendelsohn et al, 2000, *Oncogene*, 19, 6550-6565). In addition to this pre-clinical data, findings using inhibitory antibodies against EGFR and erbB2 (c-225 and trastuzumab respectively) have proven to be beneficial in the clinic for the treatment of selected solid tumours (reviewed in Mendelsohn et al, 2000, *Oncogene*, 19, 6550-6565).

Amplification and/or activity of members of the erbB type receptor tyrosine kinases have been detected and so have been implicated to play a role in a number of non-malignant proliferative disorders such as psoriasis (Ben-Bassat, *Curr. Pharm. Des.*, 2000, 6, 933; Elder et al., Science, 1989, 243, 811), benign prostatic hyperplasia (BPH) (Kumar et al., *Int. Urol. Nephrol.*, 2000, 32, 73), atherosclerosis and restenosis (Bokemeyer et al., *Kidney Int.*, 2000, 58, 549). It is therefore expected that inhibitors of erbB type receptor tyrosine kinases will be useful in the treatment of these and other non-malignant disorders of excessive cellular proliferation.

European patent application EP 566 226 discloses certain 4-anilinoquinazolines that are receptor tyrosine kinase inhibitors.

International patent applications WO 96/33977, WO 96/33978, WO 96/33979, WO 96/33980, WO 96/33981, WO 97/30034 and WO 97/38994 disclose that certain quinazoline derivatives which bear an anilino substituent at the 4-position and a substituent at the 6- and/or 7-position possess receptor tyrosine kinase inhibitory activity.

European patent application EP 837 063 discloses aryl substituted 4-aminoquinazoline derivatives carrying a moiety containing an aryl or heteroaryl group at the 6- or 7-position on the quinazoline ring. The compounds are stated to be useful for treating hyperproliferative disorders.

International patent applications WO 97/30035 and WO 98/13354 disclose certain 4-anilinoquinazolines substituted at the 7-position are vascular endothelial growth factor receptor tyrosine kinase inhibitors.

WO 00/55141 discloses 6,7-substituted 4-anilinoquinazoline compounds characterised in that the substituents at the 6- and/or 7-position carry an ester linked moiety (RO-CO).

WO 00/56720 discloses 6,7-dialkoxy-4-anilinoquinazoline compounds for the treatment of cancer or allergic reactions.

WO 02/41882 discloses 4-anilinoquinazoline compounds substituted at the 6- and/or 7-position by a substituted pyrrolidinyl-alkoxy or piperidinyl-alkoxy group.

WO 03/082290 discloses that certain 6,7-substituted 4-anilinoquinazoline compounds possess receptor tyrosine kinase inhibitory activity. A specific example of such a compound is 6-{[1-(N-methylcarbamoylmethyl)piperidin-4-yl]oxy}-4-(3-chloro-4-fluoroanilino)-7-methoxy-quinazoline.

None of the prior art discloses 4-(2,3-dihalogenoanilino) quinazoline or 4-(2,3,4-trihalogenoanilino)quinazoline compounds.

Copending International Patent Application No. PCT/GB03/01306 describes that certain 4-(2,3-dihalogenoanilino)quinazoline derivatives possess potent anti-tumour activity, and in particular are selective against EGFR. A specific example of such a compound is 6-{[1-(carbamoylmethyl)piperidin-4-yl]methoxy}-4-(3-chloro-2-fluoroanilino)-7-methoxy-quinazoline.

The applicants have surprisingly found however that addition of a substituent to the carbamoyl group and, optionally, adding a further substituent to the aniline group produces a select group of compounds with enhanced activity in that the compounds have a dual activity, being particularly effected as erbB2 kinase inhibitors, whilst retaining the EGF inhibitory effect, making them of particular clinical application in the treatment of tumours where both these kinases are implicated.

Without wishing to imply that the compounds disclosed in the present invention possess pharmacological activity only by virtue of an effect on a single biological process, it is believed that the compounds provide an anti-tumour effect by way of inhibition of two of the erbB family of receptor tyrosine kinases that are involved in the signal transduction steps which lead to the proliferation of tumour cells. In particular, it is believed that the compounds of the present invention provide an anti-tumour effect by way of inhibition of EGFR and/or erbB2 receptor tyrosine kinases.

According to a first aspect of the invention there is provided a quinazoline derivative of the Formula I:

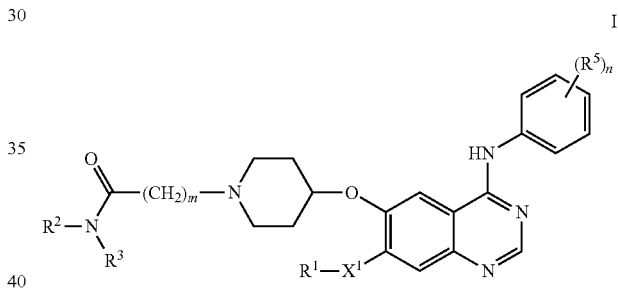

wherein n is 0, 1, 2 or 3,
each $R^5$ is independently selected from halogeno, cyano, nitro, hydroxy, amino, carboxy, sulfamoyl, trifluoromethyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylsulfamoyl, and N,N-di-[(1-6C)alkyl]sulfamoyl, $C(O)NR^6R^7$ where $R^6$ and $R^7$ are independently selected from hydrogen, optionally substituted (1-6C)alkyl, optionally substituted (3-8C)cycloalkyl or optionally substituted aryl, or $R^6$ and $R^7$ together with the nitrogen to which they are attached form an optionally substituted heterocyclic ring which may contain additional heteroatoms;
$X^1$ is a direct bond or O;
$R^1$ is selected from hydrogen and (1-6C)alkyl, wherein the (1-6C)alkyl group is optionally substituted by one or more substituents, which may be the same or different, selected from hydroxy and halogeno, and/or a substituent selected from amino, nitro, carboxy, cyano, halogeno, (1-6C)alkoxy, hydroxy(1-6C)alkoxy, (2-8C)alkenyl, (2-8C)alkynyl, (1-6C) alkylthio, (1-6C)alkylsulfinyl, (1-6C)alkylsulfonyl, (1-6C) alkylamino, di-[(1-6C)alkyl]amino, carbamoyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (1-6C)alkoxycarbonyl, sulfamoyl, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

m is 0, 1, 2 or 3;

$R^2$ is hydrogen or (1-6C)alkyl; and $R^3$ is (1-6C)alkyl, (2-6C)alkenyl, (2-6C)alkynyl or (1-6C)alkoxy, any of which can be optionally substituted on a carbon atom by a (1-6C)alkoxy, amino, (1-6C)alkylamino, di-(1-6C)alkylamino, or a group $S(O)_s$(1-6C)alkyl where s is 0, 1 or 2, or a saturated 5 or 6 membered heterocyclic ring which optionally contains additional heteroatoms selected from oxygen, sulfur or $NR^8$ where $R^8$ is hydrogen, (1-6C)alkyl, (2-6C)alkenyl, (2-6C)alkynyl, (1-6C)alkylsulfonyl or (1-6C)alkylcarbonyl;

or $R^2$ and $R^3$ together with the nitrogen atom to which they are attached form a saturated 5 or 6 membered heterocyclic ring which optionally contains additional heteroatoms selected from oxygen, S, SO or $S(O)_2$ or $NR^8$ where $R^8$ is as defined above;

provided that the quinazoline derivative is not:

4-[(3-chloro-4-fluorophenyl)amino]-6-{1-[(dimethylamino)carbonyl]-piperidin-4-yl-oxy}-7-methoxy-quinazoline;

4-[(3-chloro-4-fluorophenyl)amino]-6-{1-[(morpholin-4-yl)carbonyl]-piperidin-4-yl-oxy}-7-methoxy-quinazoline;

4-[(3-chloro-4-fluorophenyl)amino]-6-{1-[(morpholin-4-yl)carbonyl]-piperidin-4-yl-oxy}-quinazoline;

4-[(3-chloro-4-fluorophenyl)amino]-6-{1-[(dimethylamino)carbonyl]-piperidin-4-yl-oxy}-quinazoline;

4-[(3-chloro-4-fluorophenyl)amino]-6-{1-[(diethylamino)carbonyl]-piperidin-4-yl-oxy}-7-methoxy-quinazoline;

4-[(3-chloro-4-fluorophenyl)amino]-6-{1-[(piperidin-1-yl)carbonyl]-piperidin-4-yl-oxy}-7-methoxy-quinazoline;

4-[(3-chloro-4-fluorophenyl)amino]-6-{1-[(pyrrolidin-1-yl)carbonyl]-piperidin-4-yl-oxy}-7-methoxy-quinazoline;

4-[(3-chloro-4-fluorophenyl)amino]-6-{1-[(4-methyl-piperazin-1-yl)carbonyl]-piperidin-4-yl-oxy}-7-methoxy-quinazoline;

4-[(3-chloro-4-fluorophenyl)amino]-6-{1-[(morpholin-4-yl)carbonyl]piperidin-4-yl-oxy}-7-ethoxy-quinazoline;

4-[(3-chloro-4-fluorophenyl)amino]-6-{1-[(morpholin-4-yl)carbonyl]-piperidin-4-yl-oxy}-7-(2-methoxy-ethoxy)-quinazoline;

4-[(3-ethynyl-phenyl)amino]-6-{1-[(morpholin-4-yl)carbonyl]-piperidin-4-yl-oxy}-7-methoxy-quinazoline;

4-[(3-chloro-4-fluorophenyl)amino]-6-{1-[ethylamino)carbonyl]-piperidin-4-yl-oxy}-7-methoxy-quinazoline;

4-[(3-chloro-4-fluorophenyl)amino]-6-{1-[(isopropylamino)carbonyl]-piperidin-4-yl-oxy}-7-methoxy-quinazoline;

4-[(3-chloro-4-fluorophenyl)amino]-6-{1-[(dimethylamino)carbonylmethyl]-piperidin-4-yl-oxy}-quinazoline;

4-[(3-chloro-4-fluorophenyl)amino]-6-{1-[(morpholin-4-yl)carbonylmethyl]-piperidin-4-yl-oxy}-quinazoline;

4-[(3-chloro-4-fluorophenyl)amino]-6-{1-[(dimethylamino)carbonylmethyl]-piperidin-4-yl-oxy}-7-methoxy-quinazoline;

4-[(3-chloro-4-fluorophenyl)amino]-6-{1-[(morpholin-4-yl)carbonylmethyl]-piperidin-4-yl-oxy}-7-methoxy-quinazoline;

4-[(3-chloro-4-fluorophenyl)amino]-6-{1-[(methylamino)carbonylmethyl]-piperidin-4-yl-oxy}-7-methoxy-quinazoline;

4-[(3-chloro-4-fluorophenyl)amino]-6-{1-[(dimethylamino)carbonylmethyl]-piperidin-4-yl-oxy}-7-methoxy-quinazoline;

4-[(3-chloro-4-fluorophenyl)amino]-6-{1-[(pyrrolidin-1-yl)carbonylmethyl]-piperidin-4-yl-oxy}-7-methoxy-quinazoline;

4-[(3-chloro-4-fluorophenyl)amino]-6-{1-[(morpholin-4-yl)carbonylmethyl]-piperidin-4-yl-oxy}-7-methoxy-quinazoline;

4-[(3-chloro-4-fluorophenyl)amino]-6-{1-[(methylamino)carbonyl]-piperidin-4-yl-oxy}-7-methoxy-quinazoline;

4-[(3-chloro-4-fluorophenyl)amino]-6-{1-[(2-methoxyethyl)amino)carbonyl]-piperidin-4-yl-oxy}-7-methoxy-quinazoline;

4-[(3-chloro-4-fluorophenyl)amino]-6-{1-[(N-methyl-N-2-methoxyethyl)amino)carbonyl]-piperidin-4-yl-oxy}-7-methoxy-quinazoline;

4-[(3-chloro-4-fluorophenyl)amino]-6-{1-[(3-methoxypropyl)amino)carbonyl]-piperidin-4-yl-oxy}-7-methoxy-quinazoline;

4-[(3-chloro-4-fluorophenyl)amino]-6-{1-[(N-methyl-N-3-methoxypropyl)amino)carbonyl]-piperidin-4-yl-oxy}-7-methoxy-quinazoline;

4-[(3-chloro-4-fluorophenyl)amino]-6-{1-[(morpholin-4-yl)carbonylethyl]-piperidin-4-yl-oxy}-7-methoxy-quinazoline; or 4-[(3-chloro-4-fluorophenyl)amino]-6-{1-[(morpholin-4-yl)carbonylpropyl]-piperidin-4-yl-oxy}-7-methoxy-quinazoline;

or a pharmaceutically acceptable salt thereof.

In this specification the generic term "alkyl" includes both straight-chain and branched-chain alkyl groups such as propyl, isopropyl and tert-butyl, and (3-7C)cycloalkyl groups such as cyclopropyl, cyclobutyl, cyclopentyl, cyclohexyl and cycloheptyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes methoxy, ethoxy, cyclopropyloxy and cyclopentyloxy, (1-6C)alkylamino includes methylamino, ethylamino, cyclobutylamino and cyclohexylamino, and di-[(1-6Calkyl]amino includes dimethylamino, diethylamino, N-cyclobutyl-N-methylamino and N-cyclohexyl-N-ethylamino.

The term "aryl" refers to aromatic hydrocarbon rings such as phenyl or naphthyl. The terms "heterocyclic" or "heterocyclyl" include ring structures that may be mono- or bicyclic and contain from 3 to 15 atoms, at least one of which, and suitably from 1 to 4 of which, is a heteroatom such as oxygen, sulfur or nitrogen. Rings may be aromatic, non-aromatic or partially aromatic in the sense that one ring of a fused ring system may be aromatic and the other non-aromatic. Particular examples of such ring systems include furyl, benzofuranyl, tetrahydrofuryl, chromanyl, thienyl, benzothienyl, pyridyl, piperidinyl, quinolyl, 1,2,3,4-tetrahydroquinolinyl, isoquinolyl, 1,2,3,4-tetrahydroisoquinolinyl, pyrazinyl, piperazinyl, pyrimidinyl, pyridazinyl, quinoxalinyl, quinazolinyl, cinnolinyl, pyrrolyl, pyrrolidinyl, indolyl, indolinyl, imidazolyl, benzimidazolyl, pyrazolyl, indazolyl, oxazolyl, benzoxazolyl, isoxazolyl, thiazolyl, benzothiazolyl, isothiazolyl, morpholinyl, 4H-1,4-benzoxazinyl, 4H-1,4-benzothiazinyl, 1,2,3-triazolyl, 1,2,4-triazolyl, oxadiazolyl, furazanyl, thiadiazolyl, tetrazolyl, dibenzofuranyl, dibenzothienyl oxiranyl, oxetanyl, azetidinyl, tetrahydropyranyl, oxepanyl, oxazepanyl, tetrahydro-1,4-thiazinyl, 1,1-dioxotetrahydro-1,4-thiazinyl, homopiperidinyl, homopiperazinyl, dihydropyridinyl, tetrahydropyridinyl, dihydropyrimidinyl, tetrahydropyrimidinyl, tetrahydrothienyl, tetrahydrothiopyranyl or thiomorpholinyl.

Particular examples of heterocyclic groups include tetrahydropyranyl, tetrahyrdofuranyl or N-(1-6C)alkylpyrrolidine or N-alkyl(1-6C)piperidine.

Where rings include nitrogen atoms, these may carry a hydrogen atom or a substituent group such as an (1-6C)alkyl group if required to fulfil the bonding requirements of nitrogen, or they may be linked to the rest of the structure by way of the nitrogen atom. A nitrogen atom within a heterocyclyl group may be oxidized to give the corresponding N oxide.

Generally the compounds exhibit favourable physical properties such as a high solubility whilst retaining high antiproliferative activity. Furthermore, many of the compounds according to the present invention are inactive or only weakly active in a hERG assay.

It is to be understood that, insofar as certain of the compounds of Formula I defined above may exist in optically active or racemic forms by virtue of one or more asymmetrically substituted carbon and/or sulfur atoms, and accordingly may exist in, and be isolated as enantiomerically pure, a mixture of diastereoisomers or as a racemate. The present invention includes in its definition any racemic, optically-active, enantiomerically pure, mixture of diastereoisomers, stereoisomeric form of the compound of Formula I, or mixtures thereof, which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

The invention relates to all tautomeric forms of the compounds of the Formula I that possess antiproliferative activity.

It is also to be understood that certain compounds of the Formula I may exist in solvated as well as unsolvated forms such as, for example, hydrated forms. It is to be understood that the invention encompasses all such solvated forms which possess antiproliferative activity.

It is also to be understood that certain compounds of the Formula I may exhibit polymorphism, and that the invention encompasses all such forms which possess antiproliferative activity.

Suitable values for the generic radicals referred to above include those set out below.

Suitable values for any of the $R^1$, $R^2$, $R^3$ or $R^5$ groups as defined hereinbefore or hereafter in this specification include:— for halogeno fluoro, chloro, bromo and iodo;
for (1-6C)alkyl: methyl, ethyl, propyl, isopropyl, tert-butyl, pentyl and hexyl;
for (1-4C)alkyl: methyl, ethyl, propyl, isopropyl and tert-butyl;
for (1-6C)alkoxy: methoxy, ethoxy, propoxy, isopropoxy and butoxy;
for (2-8C)alkenyl: vinyl, isopropenyl, allyl and but-2-enyl;
for (2-8C)alkynyl: ethynyl, 2-propynyl and but-2-ynyl;
for (2-6C)alkenyloxy: vinyloxy and allyloxy;
for (2-6C)alkynyloxy: ethynyloxy and 2-propynyloxy;
for (1-6C)alkylthio: methylthio, ethylthio and propylthio;
for (1-6C)alkylsulfinyl: methylsulfinyl and ethylsulfinyl;
for (1-6C)alkylsulfonyl: methylsulfonyl and ethylsulfonyl;
for (1-6C)alkylamino: methylamino, ethylamino, propylamino, isopropylamino and butylamino;
for di-[(1-6C)alkyl]amino: dimethylamino, diethylamino, N-ethyl-N-methylamino and diisopropylamino;
for (1-6C)alkoxycarbonyl: methoxycarbonyl, ethoxycarbonyl, propoxycarbonyl and tert-butoxycarbonyl;
for N-(1-6C)alkylcarbamoyl: N-methylcarbamoyl, N-ethylcarbamoyl, N-propylcarbamoyl and N-isopropylcarbamoyl;
for N,N-di-[(1-6C)alkyl]carbamoyl: N,N-dimethylcarbamoyl, N-ethyl-N-methylcarbamoyl and N,N-diethylcarbamoyl;
for (2-6C)alkanoyl: acetyl, propionyl and isobutyryl;
for (2-6C)alkanoyloxy: acetoxy and propionyloxy;
for (2-6C)alkanoylamino: acetamido and propionamido;
for N-(1-6C)alkyl-(2-6C)alkanoylamino: N-methylacetamido and N-methylpropionamido;
for N-(1-6C)alkylsulfamoyl: N-methylsulfamoyl, N-ethylsulfamoyl and N-isopropylsulfamoyl;
for N,N-di-[(1-6C)alkyl]sulfamoyl: N,N-dimethylsulfamoyl and N-methyl-N-ethylsulfamoyl;
for (1-6C)alkanesulfonylamino: methanesulfonylamino and ethanesulfonylamino; for N-(1-6C)alkyl-(1-6C)alkanesulfonylamino: N-methylmethanesulfonylamino and N-methylethanesulfonylamino;
for hydroxy-(1-6C)alkoxy: hydroxymethoxy, 2-hydroxyethoxy, 1-hydroxyethoxy and 3-hydroxypropoxy.

It is to be understood that when is a group (1-6C)alkyl substituted by, for example amino to give for example a 2-aminoethyl group, it is the (1-6C)alkyl group that is attached to the group $X^1$ (or the quinazoline ring when $X^1$ is a direct bond).

When in this specification reference is made to a (1-4C) alkyl group it is to be understood that such groups refer to alkyl groups containing up to 4 carbon atoms. A skilled person will realise that representative examples of such groups are those listed above under (1-6C)alkyl that contain up to 4 carbon atoms, such as methyl, ethyl, propyl, isopropyl, butyl and tert-butyl. Similarly, reference to a (1-3C)alkyl group refers to alkyl groups containing up to 3 carbon atoms such as methyl, ethyl, propyl and isopropyl. A similar convention is adopted for the other groups listed above such as (1-4C) alkoxy, (2-4C)alkenyl, (2-4C)alkynyl and (2-4C)alkanoyl.

In the compound of Formula I hydrogen atoms are present at the 2, 5 and 8 positions on the quinazoline ring.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulfuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular examples of n are 1, 2 or 3, suitably 2 or 3.

Suitably each $R^5$ is independently selected from halogeno, trifluoromethyl, (1-6C)alkyl, (2-8C)alkenyl, (2-8C)alkynyl or a group $C(O)NR^6R^7$ where $R^6$ and $R^7$ are as defined above.

In particular, each group $R^5$ is independently selected from halogeno, such as chloro or fluoro.

Particular substituents for groups $R^6$ and $R^7$ where these are other than hydrogen, include halogeno, nitro, cyano, hydroxy, amino, carboxy, carbamoyl, sulfamoyl, trifluoromethyl, (2-8C)alkenyl, (2-8C)alkynyl, (1-6C)alkoxy, (2-6C) alkenyloxy, (2-6C)alkynyloxy, (1-6C)alkylthio, (1-6C)alkylsulfinyl, (1-6C)alkylsulfonyl, (1-6C)alkylamino, di-[(1-6C) alkyl]amino, (1-6C)alkoxycarbonyl, N-(1-6C)alkyl carbamoyl, N,N-di-[(1-6C)alkyl]carbamoyl, n-(1-6C)alkylsulfamoyl, N,N-di-[(1-6C)alkyl]sulfamoyl, (3-8C)cycloalkyl, aryl or heterocyclic groups.

Particular examples of aryl substituents for $R^6$ or $R^7$ include phenyl or naphthyl, particularly phenyl.

Particular examples of heterocyclic substituents for $R^6$ or $R^7$ include 5 or 6 membered heterocyclic rings such as furyl, tetrahydrofuryl, thienyl, pyridyl, piperidinyl, pyrazinyl, piperazinyl, pyrimidinyl, pyridazinyl, pyrrolyl, pyrrolidinyl, imidazolyl, pyrazolyl, oxazolyl, isoxazolyl, thiazolyl, isothiazolyl, morpholinyl, 1,2,3-triazolyl, 1,2,4-triazolyl, oxadiazolyl, furazanyl, thiadiazolyl or tetrazolyl.

When $R^6$ and $R^7$ together with the nitrogen to which they are attached form an optionally substituted heterocyclic ring, it is for example a 5 or 6 membered ring, which is saturated or unsaturated. Particular examples include piperidinyl, pyrrolidinyl, morpholinyl or thiomorpholino. Alternatively, $R^6$ and $R^7$ together form a (3-6C)alkenyl group.

Heterocyclic rings formed by $R^6$ and $R^7$ together with the nitrogen atom to which they are attached may be substituted by any of the groups mentioned above in relation to $R^6$ and $R^7$. In addition, these rings may be substituted by one or more (1-6C) alkyl groups, which may themselves be optionally substituted by one or more groups selected from halogeno, nitro, cyano, hydroxy, amino, carboxy, carbamoyl, sulfamoyl, trifluoromethyl, (2-8C)alkenyl, (2-8C)alkynyl, (1-6C) alkoxy, (2-6C)alkenyloxy, (2-6C)alkynyloxy, (1-6C)alkylthio, (1-6C)alkylsulfinyl, (1-6C)alkylsulfonyl, (1-6C) alkylamino, di-[(1-6C)alkyl]amino, (1-6C)alkoxycarbonyl, N-(1-6C)alkylcarbamoyl, N,N-di-[(1-6C)alkyl]carbamoyl, N-(1-6C)alkylsulfamoyl, or N,N-di-[(1-6C)alkyl]sulfamoyl.

An exemplary group of substituents for $R^6$ or $R^7$ where they are other than hydrogen are cyano, hydroxy, (2-8C)alkenyl, (2-8C)alkynyl, (1-6C)alkoxy, (1-6C)alkylthio, (1-6C)alkylamino, aryl such as phenyl or heterocyclic groups such as furyl, and additionally, where $R^6$ and $R^7$ together with the nitrogen atom to which they are attached form a ring, (1-6C) alkyl groups such as methyl.

Where n is 1, 2 or 3, one group $R^5$ is suitably at an ortho-(2-) position on the benzene ring.

Where n is 1, 2 or 3, one group $R^5$ is suitably at a meta-(3-) position on the benzene ring.

Thus, when n is 1, the $R^5$ group is suitably at an ortho-(2-) or a meta-(3-) position on the benzene ring.

In one aspect of the invention, when n is 2, the first $R^5$ group is suitably at a meta-position and the second $R^5$ group is suitably at an ortho- or a para-position on the benzene ring, and thus the ring has substituents at 2- and 3- or 3- and 4-positions on the benzene ring.

In another aspect of the invention, when n is 2 or 3, the first $R^5$ group is suitably at an ortho-position, the second $R^5$ group is suitably at a meta-position and, optionally (when n is 3), the third $R^5$ group is suitably at a para-position on the benzene ring. Thus, when n is 2, the ring suitably has substituents at 2- and 3-positions on the benzene ring and when n is 3, the ring suitably has substituents at 2-, 3- and 4-positions on the benzene ring.

The applicants have surprisingly found that quinazoline derivatives having substituents (for example halogeno substituents) at 2- and 3-positions or at 2-, 3- and 4-positions on the benzene ring compared to quinazoline derivatives having substituents at 3- and 4-positions on the benzene ring produces compounds with enhanced activity in that the compounds have an increased potency against erbB2 and/or EGFR (particularly erbB2) receptor tyrosine kinases in cellular assays. It is believed that quinazoline derivatives having substituents (for example halogeno substituents) at 2- and 3-positions or at 2-, 3- and 4-positions on the benzene ring will also have an increased potency against erbB2 and/or EGFR (particularly erbB2) receptor tyrosine kinases in vivo.

Suitably when n is 2 or 3, each $R^5$ group is the same or different halogeno atom, such as chloro or fluoro. Suitably, at least one $R^5$ group is fluoro, which at least one fluoro is preferably positioned at an ortho-(2-) position on the benzene ring.

Suitably when n is 2, each $R^5$ group is the same or different halogeno atom. In particular, one $R^5$ group is chloro, and this is preferably at a meta-(3-) position on the benzene ring to which it is attached, and the other $R^5$ group is fluoro which is preferably at an ortho-(2-) or a para-(4-) (preferably an ortho-(2-)) position on the benzene ring.

Suitably when n is 3, each $R^5$ group is the same or different halogeno atom. In particular, one $R^5$ group is chloro, and this is preferably at a meta-(3-) position on the benzene ring to which it is attached, and the other two $R^5$ groups are each fluoro, which are preferably at an ortho-(2-) and a para-(4-) position respectively on the benzene ring.

Thus particular examples of the group of sub-formula (i):

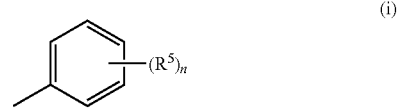

(i)

in Formula I are groups of sub-formula (ii):

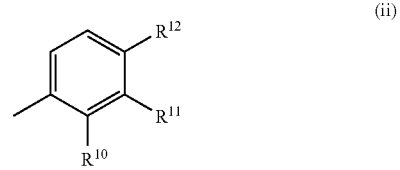

(ii)

wherein (a) one of $R^{10}$ or $R^{12}$ is hydrogen and the other is halogeno, such as chloro or fluoro, and particularly fluoro, and $R^{11}$ is halogeno such as chloro or fluoro, and particularly chloro, or (b) $R^{10}$ is halogeno, such as chloro or fluoro, and particularly fluoro, $R^{11}$ is halogeno such as chloro or fluoro, and particularly chloro, and $R^{12}$ is hydrogen or halogeno, such as chloro or fluoro, and particularly fluoro, or (c) $R^{10}$ is fluoro, $R^{11}$ is chloro, and $R^{12}$ is hydrogen or fluoro. In particular, $R^{10}$, $R^{11}$ and $R^{12}$ are as defined in (b) and/or (c).

In one embodiment, when n is 2, each $R^5$ group is the same or different halogeno atom (such as fluoro and/or chloro) and the first $R^S$ group is at an ortho-position and the second $R^5$ group is at a meta-position on the benzene ring, then (i) when m is 0, 1, 2 or 3, $R^3$ is not (1-6C)alkyl and (ii) when m is 0, $R^2$ and $R^3$ do not, together with the nitrogen atom to which they are attached, form a saturated 5 or 6 membered heterocyclic ring which optionally contains additional heteroatoms selected from oxygen, S, SO or $S(O)_2$ or $NR^8$ where $R^8$ is hydrogen, (1-4C)alkyl or (1-4C)alkylsulfonyl.

Suitably $X^1$ is oxygen.

In particular $R^1$ is selected from hydrogen, (1-6C)alkyl and (1-6C)alkoxy(1-6C)alkyl, wherein any (1-6C)alkyl group in $R^1$ optionally bears one or more (suitably 1 or 2) hydroxy or halogeno substituents. More particularly, $R^1$ is selected from (1-6C)alkyl, preferably from (1-4C)alkyl and even more preferably from (1-2C)alkyl. For example, $R^1$ may be methyl.

For instance, $R^1$—$X^1$— is selected from methoxy, ethoxy, isopropyloxy, cyclopropylmethoxy, 2-hydroxyethoxy, 2-fluoroethoxy, 2-methoxyethoxy, 2,2-difluoroethoxy, 2,2,2-trifluoroethoxy or 3-hydroxy-3-methylbutoxy.

In particular $R^1$—X— is selected from hydrogen, (1-4C)alkoxy and (1-4C)alkoxy(1-4C)alkoxy. For instance, $R^1$—X— is selected from hydrogen, methoxy, ethoxy and 2-methoxyethoxy. A particular example of a group $R^1$—$X^1$— is methoxy.

Suitably m is 1, 2 or 3. Preferably m is 0 or 1 (more preferably 1).

When $R^2$ and $R^3$ together with the nitrogen atom to which they are attached form a saturated heterocyclic ring which optionally contains additional heteroatoms, the heterocyclic ring is particularly a 6 membered ring.

When $R^2$ and $R^3$ together with the nitrogen atom to which they are attached form a saturated 5 or 6 (preferably 6) membered heterocyclic ring which optionally contains additional heteroatoms, this suitably contains additional heteroatoms selected from O and $NR^8$, where $R^8$ is as defined in relation to Formula I.

When $R^2$ and $R^3$ together with the nitrogen atom to which they are attached form a saturated 5 or 6 membered heterocyclic ring which optionally contains additional heteroatoms, this suitably comprises a pyrrolidine ring, a morpholine ring, a piperidine ring, or a piperazine ring which is optionally substituted on the available nitrogen atom by a group $R^8$ as defined above. In particular, the heterocyclic ring comprises a morpholine ring or a piperazine ring which is optionally substituted on the available nitrogen atom by a group $R^8$ as defined in relation to Formula I.

Particular examples of $R^8$ groups include (1-3C) alkyl such as methyl; (1-3C)alkylsulfonyl such as methylsulfonyl; (1-3C)alkylcarbonyl, such as acetyl; (2-4C)alkenyl such as allyl; or (2-4C)alkynyl such as propargyl. In particular $R^8$ is a (1-3C)alkyl group such as methyl.

Thus when $R^2$ together with $R^3$ together with the nitrogen atom to which they are attached form a saturated 5 or 6 membered heterocyclic ring which optionally contains additional heteroatoms, this suitably comprises a morpholine ring. Other examples include pyrrolidine, piperidine, piperazine or N-methylpiperazine, particularly piperazine or N-methylpiperazine.

Preferably $R^2$ is hydrogen or (1-3C)alkyl.

In particular $R^2$ is hydrogen or methyl (preferably hydrogen).

Suitable substituents for $R^3$ include (1-6C)alkoxy, (1-6C)alkylamino, di-(1-6C)alkylamino or a saturated 5 or 6 membered heterocyclic ring which optionally contains additional heteroatoms selected from oxygen, sulfur or $NR^8$ where $R^8$ is as defined above.

In particular, suitable substituents for $R^3$ include (1-3C) alkoxy such as methoxy, amino, (1-3C)alkylamino, di-(1-3C) alkylamino such as dimethylamino, (1-3C)alkylsulfonyl, a pyrrolidine ring or a piperazine ring, which may contain on the available nitrogen atom a (1-3C)alkyl group such as methyl, a (24C)alkenyl group such as vinyl, an (2-4C)alkynyl group such as propargyl, an (1-5C)alkylsulfonyl group such as methyl sulfonyl or an (1-6C)alkylcarbonyl group such as acetyl.

Suitably $R^3$ is (1-6C)alkyl, in particular (1-3C)alkyl, such as methyl or ethyl. Suitably $R^2$ is hydrogen and $R^3$ is (1-6C) alkyl, in particular (1-3C)alkyl, such as methyl or ethyl.

Particular examples of the compounds of Formula I are compounds of Formula IA:

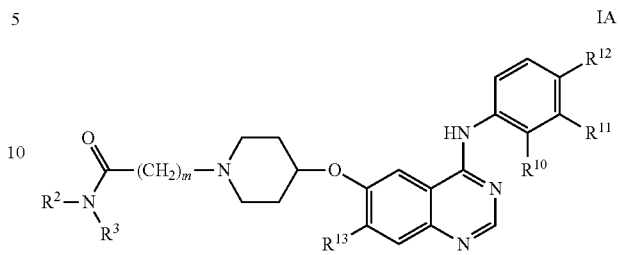

IA where $R^2$, $R^3$ and m are as defined above, $R^{10}$, $R^{11}$ and $R^{12}$ are as defined in relation to sub-formula (ii) above, and $R^{13}$ is selected from hydrogen, methoxy, ethoxy and 2-methoxyethoxy, and especially methoxy.

For the avoidance of any doubt, when the compounds of Formula I are defined as compounds of Formula IA, the quinazoline derivative is not:

4-[(3-chloro-4-fluorophenyl)amino]-6-{1-[((dimethylamino)carbonyl]-piperidin-4-yl-oxy}-7-methoxy-quinazoline;

4-[(3-chloro-4-fluorophenyl)amino]-6-{1-[(morpholin-4-yl) carbonyl]-piperidin-4-yl-oxy}-7-methoxy-quinazoline;

4-[(3-chloro-4-fluorophenyl)amino]-6-{1-[(morpholin-4-yl) carbonyl]-piperidin-4-yl-oxy}-quinazoline;

4-[(3-chloro-4-fluorophenyl)amino]-6-{4[dimethylamino) carbonyl]-piperidin-4-yl-oxy}-quinazoline;

4-[(3-chloro-4-fluorophenyl)amino]-6-{1-[(diethylamino) carbonyl]-piperidin-4-yl-oxy}-7-methoxy-quinazoline;

4-[(3-chloro-4-fluorophenyl)amino]-6-{1-[(piperidin-1-yl) carbonyl]-piperidin-4-yl-oxy}-7-methoxy-quinazoline;

4-[(3-chloro-4-fluorophenyl)amino]-6-{1-[(pyrrolidin-1-yl) carbonyl]-piperidin-4-yl-oxy}-7-methoxy-quinazoline;

4-[(3-chloro-4-fluorophenyl)amino]-6-{1-[(4-methyl-piperazin-1-yl)carbonyl]-piperidin-4-yl-oxy}-7-methoxy-quinazoline;

4-[(3-chloro-4-fluorophenyl)amino]-6-{1-[(morpholin-4-yl)carbonyl]-piperidin-4-yl-oxy}-7-ethoxy-quinazoline;

4-[(3-chloro-4-fluorophenyl)amino]-6-{1-[(morpholin-4-yl) carbonyl]-piperidin-4-yl-oxy}-7-(2-methoxy-ethoxy)-quinazoline;

4-[(3-chloro-4-fluorophenyl)amino]-6-{(1-[(ethylamino) carbonyl]-piperidin-4-yl-oxy}-7-methoxy-quinazoline;

4-[(3-chloro-4-fluorophenyl)amino]-6-{1-[(isopropylamino)carbonyl]-piperidin-4-yl-oxy}-7-methoxy-quinazoline;

4-[(3-chloro-4-fluorophenyl)amino]-6-{(1-[(dimethylamino)carbonylmethyl]-piperidin-4-yl-oxy}-quinazoline;

4-[(3-chloro-4-fluorophenyl)amino]-6-{1-[(morpholin-4-yl) carbonylmethyl]-piperidin-4-yl-oxy}-quinazoline;

4-[(3-chloro-4-fluorophenyl)amino]-6-{1-[(dimethylamino) carbonylmethyl]-piperidin-4-yl-oxy}-7-methoxy-quinazoline;

4-[(3-chloro-4-fluorophenyl)amino]-6-{1-[(morpholin-4-yl) carbonylmethyl]-piperidin-4-yl-oxy}-7-methoxy-quinazoline;

4-[(3-chloro-4-fluorophenyl)amino]-6-{1-[(methylamino) carbonylmethyl]-piperidin-4-yl-oxy}-7-methoxy-quinazoline;

4-[(3-chloro-4-fluorophenyl)amino]-6-{1-[(dimethylamino) carbonylmethyl]-piperidin-4-yl-oxy}-7-methoxy-quinazoline;

4-[(3-chloro-4-fluorophenyl)amino]-6-{1-[(pyrrolidin-1-yl)carbonylmethyl]-piperidin-4-yl-oxy}-7-methoxy-quinazoline;

4-[(3-chloro-4-fluorophenyl)amino]-6-{1-[(morpholin-4-yl)carbonylmethyl]-piperidin-4-yl-oxy}-7-methoxy-quinazoline;

4-[(3-chloro-4-fluorophenyl)amino]-6-{1-[(methylamino)carbonyl]-piperidin-4-yl-oxy}-7-methoxy-quinazoline;

4-[(3-chloro-4-fluorophenyl)amino]-6-{1-[(2-methoxyethyl)amino)carbonyl]-piperidin-4-yl-oxy}-7-methoxy-quinazoline;

4-[(3-chloro-4-fluorophenyl)amino]-6-{1-[(N-methyl-N-2-methoxyethyl)amino)carbonyl]-piperidin-4-yl-oxy}-7-methoxy-quinazoline;

4-[(3-chloro-4-fluorophenyl)amino]-6-{1-[(3-methoxypropyl)amino)carbonyl]-piperidin-4-yl-oxy}-7-methoxy-quinazoline;

4-[(3-chloro-4-fluorophenyl)amino]-6-{1-[(N-methyl-N-3-methoxypropyl)amino)carbonyl]-piperidin-4-yl-oxy}-7-methoxy-quinazoline;

4-[(3-chloro-4-fluorophenyl)amino]-6-{1-[(morpholin-4-yl)carbonylethyl]-piperidin-4-yl-oxy}-7-methoxy-quinazoline; or 4-[(3-chloro-4-fluorophenyl)amino]-6-{1-[(morpholin-4-yl)carbonylpropyl]-piperidin-4-yl-oxy}-7-methoxy-quinazoline;

or a pharmaceutically acceptable salt thereof.

Other particular examples of the compounds of Formula I are compounds of the Formulae IB and IC:

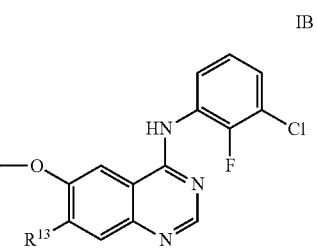

IB

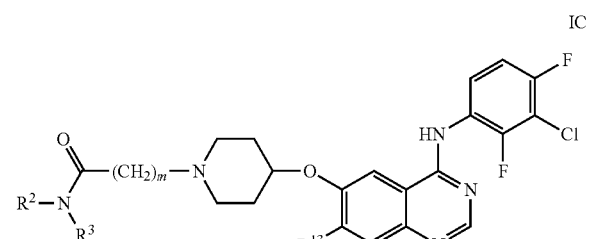

IC where $R^2$, $R^3$ and m are as defined above and $R^{13}$ is selected from hydrogen, methoxy, ethoxy and 2-methoxyethoxy, and especially methoxy.

Other particular examples of the compounds of Formula I are compounds of the Formula ID:

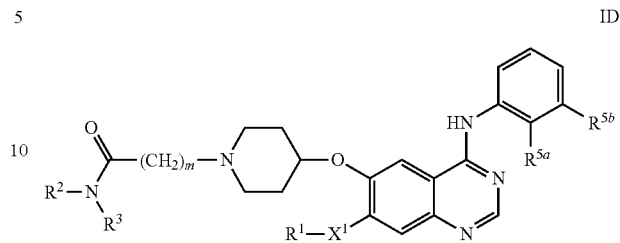

ID wherein:

$R^{5a}$ and $R^{5b}$ are independently selected from halogeno (for example fluoro and/or chloro);

$X^1$ is a direct bond or O;

$R^1$ is selected from hydrogen and (1-6C)alkyl, wherein the (1-6C)alkyl group is optionally substituted by one or more substituents, which may be the same or different, selected from hydroxy and halogeno, and/or a substituent selected from amino, nitro, carboxy, cyano, halogeno, (1-6C)alkoxy, hydroxy(1-6C)alkoxy, (2-8C)alkenyl, (2-8C)alkynyl, (1-6C)alkylthio, (1-6C)alkylsulfinyl, (1-6C)alkylsulfonyl, (1-6C)alkylamino, di-[(1-6C)alkyl]amino, carbamoyl, N-(1-6C)alkylcarbamoyl, N,N di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (1-6C)alkoxycarbonyl, sulfamoyl, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

m is 0, 1, 2 or 3;

$R^2$ is hydrogen or (1-6C)alkyl; and $R^3$ is (1-6C)alkyl, wherein the (1-6C)alkyl group is optionally substituted on a carbon atom by a (1-6C)alkoxy, amino, (1-6C)alkylamino, di-(1-6C)alkylamino, or a group $S(O)_s$(1-6C)alkyl where s is 0, 1 or 2, or a saturated 5 or 6 membered heterocyclic ring which optionally contains additional heteroatoms selected from oxygen, sulfur or $NR^8$ where $R^8$ is hydrogen, (1-6C)alkyl, (2-6C)alkenyl, (2-6C)alkynyl, (1-6C)alkylsulfonyl or (1-6C)alkylcarbonyl; or when m is 0, $R^2$ and $R^3$ together with the nitrogen atom to which they are attached form a saturated 5 or 6 membered heterocyclic ring which optionally contains additional heteroatoms selected from oxygen, S, SO or $S(O)_2$ or $NR^8$ where $R^8$ is hydrogen, (1-4C)alkyl or (1-4C)alkylsulfonyl;

or a pharmaceutically acceptable salt thereof.

In one embodiment of the compounds of the Formula ID, the group $R^3$ is (1-6C)alkyl, particularly unsubstituted (1-6C)alkyl. For example, the group $R^3$ may be methyl or ethyl, particularly methyl.

In another embodiment of the compounds of the Formula ID, m is 0 and $R^2$ and $R^3$ together with the nitrogen atom to which they are attached form a saturated 5 or 6 membered heterocyclic ring which optionally contains additional heteroatoms selected from oxygen, S, SO or $S(O)_2$ or $NR^8$ where $R^8$ is hydrogen, (1-4C)alkyl or (1-4C)alkylsulfonyl. For example, $R^2$ together with $R^3$ together with the nitrogen atom to which they are attached may form a morpholine ring. Other examples include pyrrolidine, piperidine, piperazine or N-methylpiperazine, particularly piperazine or N-methylpiperazine.

It would be clear to a person skilled in the an that the particular novel compounds of the invention include those compounds of the Formula I (including IA, IB, IC and ID) in which, unless otherwise stated, each of $R^1$, $R^2$, $R^3$, $R^5$, $X^1$, m and n has any of the meanings as hereinbefore defined.

Examples of quinazoline derivatives of the Formula I include one or more of:

4-(3-chloro-2-fluoroanilino)-7-methoxy-6-{[1-(N-methylcarbamoylmethyl)piperidin-4-yl]-oxy}quinazoline;

4-(3-chloro-2-fluoroanilino)-6-{[1-(N,N-dimethylcarbamoylmethyl)piperidin-4-yl]oxy}-7-methoxyquinazoline;

4-(3-chloro-2-fluoroanilino)-7-methoxy-6-{[1-(morpholin-4-ylcarbonylmethyl)piperidin-4-yl]oxy}-quinazoline;

4-(3-chloro-2-fluoroanilino)-7-methoxy-6-{[1-(pyrrolidin-1-ylcarbonyl)piperidin-4-yl]oxy}quinazoline;

4-(3-chloro-2-fluoroanilino)-7-methoxy-6-{[1-(N-methylcarbamoyl)piperidin-4-yl]oxy}quinazoline;

4-(3-chloro-2-fluoroanilino)-6-{[1-(N-(2-dimethylaminoethyl)carbamoyl)piperidin-4-yl]oxy)}-7-methoxyquinazoline;

4-(3-chloro-2-fluoroanilino)-6-{[1-(N,N-dimethylcarbamoyl)piperidin-4-yl]oxy}-7-methoxy-quinazoline;

4-(3-chloro-2-fluoroanilino)-7-methoxy-6-{[1-(morpholin-4-ylcarbonyl)piperidin-4-yl]oxy}quinazoline;

4-(3-chloro-2-fluoroanilino)-7-methoxy-6-{[1-(N-[2-pyrrolidin-1-ylethyl]carbamoyl) piperidin-4-yl]oxy}quinazoline;

4-(3-chloro-2,4-difluoroanilino)-7-methoxy-6-{[1-(N-methylcarbarnoylmethyl)piperidin-4-yl]oxy}quinazoline;

4-(3-chloro-2-fluoroanilino)-6-{[1-(N-ethylcarbamoylmethyl)piperidin-4-yl]oxy}-7-methoxyquinazoline;

4-(3-chloro-2-fluoroanilino)-7-methoxy-6-{[1-(N-[2-(pyrrolidin-1-yl)ethyl]carbamoylmethyl)piperidin-4-yl]oxy}quinazoline;

4-(3-chloro-2-fluoroanilino)-7-methoxy-6-{[1-(N-(2-methoxyethyl)carbamoylmethyl)piperidin-4-yl]oxy}quinazoline;

4-(3-chloro-2-fluoroanilino)-6-{[1-(N-(2-dimethylaminoethyl)carbamoylmethyl)piperidin-4-yl]oxy}-7-methoxyquinazoline;

4-(3-chloro-2-fluoroanilino)-7-methoxy-6-({1-[2-(4-methylpiperazin-1-yl)-2-oxoethyl]piperidin-4-yl}oxy)quinazoline;

4-(3-chloro-2-fluoroanilino)-7-methoxy-6-({1-[2-(piperazin-1-yl)-2-oxoethyl]piperidin-4-yl}oxy)quinazoline; and 4-(3-chloro-2,4-difluoroanilino)-7-methoxy-6-({1-[2-(4-methylpiperazin-1-yl)-2-oxoethyl]piperidin-4-yl}oxy)quinazoline;

or a pharmaceutically acceptable salt thereof.

Particular examples of quinazoline derivatives of the Formula I include one or more of:

4-(3-chloro-2-fluoroanilino)-7-methoxy-6-{[1-(N-methylcarbamoylmethyl)piperidin-4-yl]-oxy}quinazoline;

4-(3-chloro-2-fluoroanilino)-7-methoxy-6-{[1-(N-methylcarbamoyl)piperidin-4-yl]oxy}quinazoline;

4-(3-chloro-2-fluoroanilino)-7-methoxy-6-{[1-(morpholin-4-ylcarbonyl)piperidin-4-yl]oxy}quinazoline;

4-(3-chloro-2-fluoroanilino)-7-methoxy-6-{[1-(N-[2-pyrrolidin-1-ylethyl]carbamoyl) piperidin-4-yl]oxy}quinazoline;

4-(3-chloro-2,4-difluoroanilino)-7-methoxy-6-{[1-(N-methylcarbamoylmethyl)piperidin-4-yl]oxy}quinazoline;

4-(3-chloro-2-fluoroanilino)-6-{[1-(N-ethylcarbamoylmethyl)piperidin-4-yl]oxy}-7-methoxyquinazoline;

4-(3-chloro-2-fluoroanilino)-7-methoxy-6-{[1-(N-[2-(pyrrolidin-1-yl)ethyl]carbamoylmethyl)piperidin-4-yl]oxy}quinazoline;

4-(3-chloro-2-fluoroanilino)-7-methoxy-6-{[1-(N-(2-methoxyethyl)carbamoylmethyl)piperidin-4-yl]oxy}quinazoline;

4-(3-chloro-2-fluoroanilino)-6-{[1-(N-(2-dimethylaminoethyl)carbamoylmethyl)piperidin-4-yl]oxy}-7-methoxyquinazoline;

4-(3-chloro-2-fluoroanilino)-7-methoxy-6-({1-[2-(4-methylpiperazin-1-yl)-2-oxoethyl]piperidin-4-yl}oxy)quinazoline;

4-(3-chloro-2-fluoroanilino)-7-methoxy-6-({1-[2-(piperazin-1-yl)-2-oxoethyl]piperidin-4-yl}oxy)quinazoline; and 4-(3-chloro-2,4-difluoroanilino)-7-methoxy-6-({1-[2-(4-methylpiperazin-1-yl)-2-oxoethyl]piperidin-4-yl}oxy)quinazoline;

or a pharmaceutically acceptable salt thereof.

A particular group of examples of quinazoline derivatives of the Formula I includes one or more of:

4-(3-chloro-2-fluoroanilino)-7-methoxy-6-{[1-(N-methylcarbamoylmethyl)piperidin-4-yl]oxy}quinazoline; and 4-(3-chloro-2,4-difluoroanilino)-7-methoxy-6-{[1-(N-methylcarbamoylmethyl)piperidin-4-yl]oxy}quinazoline;

or a pharmaceutically acceptable salt thereof.

A particular group of examples of quinazoline derivatives of the Formula IB includes one or more of:

4-(3-chloro-2-fluoroanilino)-7-methoxy-6-{[1-(N-methylcarbamoylmethyl)piperidin-4-yl]-oxy}quinazoline;

4-(3-chloro-2-fluoroanilino)-6-{[1-(N,N-dimethylcarbamoylmethyl)piperidin-4-yl]oxy}-7-methoxyquinazoline;

4-(3-chloro-2-fluoroanilino)-7-methoxy-6-{[1-(morpholin-4-ylcarbonylmethyl)piperidin-4-yl]oxy}-quinazoline;

4-(3-chloro-2-fluoroanilino)-7-methoxy-6-{[1-(pyrrolidin-1-ylcarbonyl)piperidin-4-yl]oxy}quinazoline;

4-(3-chloro-2-fluoroanilino)-7-methoxy-6-{[1-(N-methylcarbamoyl)piperidin-4-yl]oxy}quinazoline;

4-(3-chloro-2-fluoroanilino)-6-{[1-(N-(2-dimethylaminoethyl)carbamoyl)piperidin-4-yl]oxy}-7-methoxyquinazoline;

4-(3-chloro-2-fluoroanilino)-6-{[1-(N,N-dimethylcarbamoyl)piperidin-4-yl]oxy}7-methoxy-quinazoline;

4-(3-chloro-2-fluoroanilino)-7-methoxy-6-{[1-(morpholin-4-ylcarbonyl)piperidin-4-yl]oxy}quinazoline;

4-(3-chloro-2-fluoroanilino)-7-methoxy-6-{[1-(N-[2-pyrrolidin-1-ylethyl]carbamoyl) piperidin-4-yl]oxy}quinazoline;

4-(3-chloro-2-fluoroanilino)-6-{[1-(N-ethylcarbamoylmethyl)piperidin-4-yl]oxy}-7-methoxyquinazoline;

4-(3-chloro-2-fluoroanilino)-7-methoxy-6-{[1-(N-[2-(pyrrolidin-1-yl)ethyl]carbamoylmethyl)piperidin-4-yl]oxy}quinazoline;

4-(3-chloro-2-fluoroanilino)-7-methoxy-6-{[1-(N-(2-methoxyethyl)carbamoylmethyl)piperidin-4-yl]oxy}quinazoline;

4-(3-chloro-2-fluoroanilino)-6-{[1-(N-(2-dimethylaminoethyl)carbamoylmethyl)piperidin-4-yl]oxy}-7-methoxyquinazoline;

4-(3-chloro-2-fluoroanilino)-7-methoxy-6-({1-[2-(4-methylpiperazin-1-yl)-2-oxoethyl]piperidin-4-yl}oxy)quinazoline; and 4-(3-chloro-2-fluoroanilino)-7-methoxy-6-({1-[2-(piperazin-1-yl)-2-oxoethyl]piperidin-4-yl}oxy)quinazoline;

or a pharmaceutically acceptable salt thereof.

A particular group of examples of quinazoline derivatives of the Formula IC includes one or more of:

4-(3-chloro-2,4-difluoroanilino)-7-methoxy-6-{[1-(N-methylcarbamoylmethyl)piperidin-4-yl]oxy}quinazoline; and 4-(3-chloro-2,4-difluoroanilino)-7-methoxy-6-({1-[2-(4-methylpiperazin-1-yl)-2-oxoethyl]piperidin-4-yl}oxy)quinazoline;

or a pharmaceutically acceptable salt thereof.

A particular group of examples of quinazoline derivatives of the Formula ID includes one or more of:

4-(3-chloro-2-fluoroanilino)-7-methoxy-6-{[1-(N-methylcarbamoylmethyl)piperidin-4-yl]-oxy}quinazoline;

4-(3-chloro-2-fluoroanilino)-6-{[1-(N,N-dimethylcarbamoylmethyl)piperidin-4-yl]oxy}-7-methoxyquinazoline;

4-(3-chloro-2-fluoroanilino)-7-methoxy-6-{[1-(pyrrolidin-1-ylcarbonyl)piperidin-4-yl]oxy}quinazoline;

4-(3-chloro-2-fluoroanilino)-7-methoxy-6-{[1-(N-methylcarbamoyl)piperidin-4-yl]oxy}quinazoline;

4-(3-chloro-2-fluoroanilino)-6-{[1-(N-(2-dimethylaminoethyl)carbamoyl)piperidin-4-yl]oxy}-7-methoxyquinazoline;

4-(3-chloro-2-fluoroanilino)-6-{[1-(N,N-dimethylcarbamoyl)piperidin-4-yl]oxy}-7-methoxy-quinazoline;

4-(3-chloro-2-fluoroanilino)-7-methoxy-6-{[1-(morpholin-4-ylcarbonyl)piperidin-4-yl]oxy}quinazoline;

4-(3-chloro-2-fluoroanilino)-7-methoxy-6-{[1-(N-[2-pyrrolidin-1-ylethyl]carbamoyl)piperidin-4-yl]oxy}quinazoline;

4-(3-chloro-2-fluoroanilino)-6-{[1-(N-ethylcarbamoylmethyl)piperidin-4-yl]oxy}-7-methoxyquinazoline;

4-(3-chloro-2-fluoroanilino)-7-methoxy-6-{[1-(N-[2-(pyrrolidin-1-yl)ethyl]carbamoylmethyl)piperidin-4-yl]oxy}quinazoline;

4-(3-chloro-2-fluoroanilino)-7-methoxy-6-{[1-(N-(2-methoxyethyl)carbamoylmethyl)piperidin-4-yl]oxy}quinazoline; and 4-(3-chloro-2-fluoroanilino)-6-{[1-(N-(2-dimethylaminoethyl)carbamoylmethyl)piperidin-4-yl]oxy}-7-methoxyquinazoline;

or a pharmaceutically acceptable salt thereof.

Another particular group of examples of quinazoline derivatives of the Formula ID includes one or more of:

4-(3-chloro-2-fluoroanilino)-7-methoxy-6-{[1-(N-methylcarbamoylmethyl)piperidin-4-yl]-oxy}quinazoline;

4-(3-chloro-2-fluoroanilino)-6-{[1-(N,N-dimethylcarbamoylmethyl)piperidin-4-yl]oxy}-7-methoxyquinazoline;

4-(3-chloro-2-fluoroanilino)-7-methoxy-6-{[1-(pyrrolidin-1-ylcarbonyl)piperidin-4-yl]oxy}quinazoline;

4-(3-chloro-2-fluoroanilino)-7-methoxy-6-{[1-(N-methylcarbamoyl)piperidin-4-yl]oxy}quinazoline;

4-(3-chloro-2-fluoroanilino)-6-{[1-(N,N-dimethylcarbamoyl)piperidin-4-yl]oxy}-7-methoxy-quinazoline;

4-(3-chloro-2-fluoroanilino)-7-methoxy-6-{[1-(morpholin-4-ylcarbonyl)piperidin-4-yl]oxy}quinazoline; and 4-(3-chloro-2-fluoroanilino)-6-{[1-(N-ethylcarbamoylmethyl)piperidin-4-yl]oxy}-7-methoxyquinazoline;

or a pharmaceutically acceptable salt thereof.

A preferred example of a compound of the Formula I is 4-(3-chloro-2-fluoroanilino)-7-methoxy-6-{[1-(N-methylcarbamoylmethyl)piperidin-4-yl]oxy}quinazoline, or a pharmaceutically acceptable salt thereof.

Another preferred example of a compound of the Formula I is 4-(3-chloro-2,4-difluoroanilino)-7-methoxy-6-{[1-(N-methylcarbamoylmethyl)piperidin-4-yl]oxy}quinazoline, or a pharmaceutically acceptable salt thereof.

Another preferred example of a compound of the Formula I is 4-(3-chloro-2-fluoroanilino)-7-methoxy-6-{[1-(N-[2-(pyrrolidin-1-yl)ethyl]carbamoylmethyl)piperidin-4-yl]oxy}quinazoline, or a pharmaceutically acceptable salt thereof.

Another preferred example of a compound of the Formula I is 4-(3-chloro-2-fluoroanilino)-7-methoxy-6-({1-[2-(4-methylpiperazin-1-yl)-2-oxoethyl]piperidin-4-yl}oxy)quinazoline, or a pharmaceutically acceptable salt thereof.

Another preferred example of a compound of the Formula I is 4-(3-chloro-2-fluoroanilino)-7-methoxy-6-({1-[2-(piperazin-1-yl)-2-oxoethyl]piperidin-4-yl}oxy)quinazoline, or a pharmaceutically acceptable salt thereof.

Synthesis of Quinazoline Derivatives of the Formula I

A further aspect the present invention provides a process for preparing a quinazoline derivative of Formula I or a pharmaceutically-acceptable salt thereof. It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher. John Wiley & Sons). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art.

A quinazoline derivative of the Formula I, or a pharmaceutically-acceptable salt thereof, may be prepared by any process known to be applicable to the preparation of chemically-related compounds. Such processes, when used to prepare a quinazoline derivative of the Formula I, or a pharmaceutically-acceptable salt thereof, are provided as a further feature of the invention and are illustrated by the following representative examples. Necessary starting materials may be obtained by standard procedures of organic chemistry (see, for example, Advanced Organic Chemistry (Wiley-Interscience), Jerry March). The preparation of such starting materials is described within the accompanying non-limiting Examples. Alternatively, necessary starting materials are obtainable by analogous procedures to those illustrated which are within the ordinary skill of an organic chemist. Information on the preparation of necessary starting materials or related compounds (which may be adapted to form necessary starting materials) may also be found in the following Patent and Application Publications, the contents of the relevant process sections of which are hereby incorporated herein by reference: WO 94/27965, WO 95/03283, WO 96/33977, WO 96/33978, WO 96/33979, WO 96/33980, WO 96/33981, WO 97/30034, WO 97/38994, WO 01/66099, U.S. Pat. No. 5,252, 586, EP 520 722; EP 566 226, EP 602 851 and EP 635 507.

The present invention also provides that quinazoline derivatives of the Formula I, or pharmaceutically acceptable salts thereof, can be prepared by a process (a) to (m) as follows (wherein the variables are as defined above unless otherwise stated):

Process (a) By reacting a compound of the Formula II:

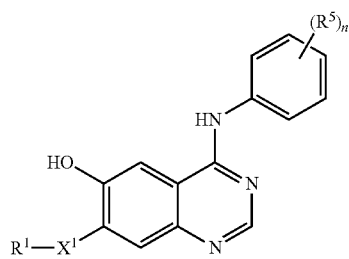

wherein $R^1$, $X^1$, $R^5$ and n have any of the meanings defined hereinbefore except that any functional group is protected if necessary, with a compound of the Formula III:

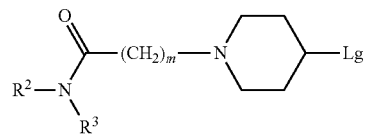

wherein $R^2$, $R^3$ and m have any of the meanings defined hereinbefore except that any functional group is protected if necessary and Lg is a displaceable group, wherein the reaction is conveniently performed in the presence of a suitable base, and whereafter any protecting group that is present is removed by conventional means.

A convenient displaceable group Lg is, for example, a halogeno, alkanesulfonyloxy or arylsulfonyloxy group, for example a chloro, bromo, methanesulfonyloxy, 4-nitrobenzenesulfonyloxy or toluene-4-sulfonyloxy group (suitably a methanesulfonyloxy, 4-nitrobenzenesulfonyloxy or toluene-4-sulfonyloxy group).

The reaction is advantageously carried out in the presence of base. A suitable base is, for example, an organic amine base such as, for example, di-isopropylethylamine, pyridine, 2,6-lutidine, collidine, 4-dimethylaminopyridine, triethylamine, N-methylmorpholine or diazabicyclo[5.4.0]undec-7-ene, or for example, an alkali metal or alkaline earth metal carbonate or hydroxide, for example sodium carbonate, potassium carbonate, cesium carbonate, calcium carbonate, sodium hydroxide or potassium hydroxide. Alternatively such a base is, for example, an alkali metal hydride, for example sodium hydride, an alkali metal or alkaline earth metal amide, for example sodium amide or sodium bis(trimethylsilyl)amide, or a sufficiently basic alkali metal halide, for example cesium fluoride or sodium iodide. The reaction is suitably effected in the presence of an inert solvent or diluent, for example an alkanol or ester such as methanol, ethanol, 2-propanol or ethyl acetate, a halogenated solvent such as methylene chloride, trichloromethane or carbon tetrachloride, an ether such as tetrahydrofuran or 1,4-dioxan, an aromatic hydrocarbon solvent such as toluene, or (suitably) a dipolar aprotic solvent such as N,N-dimethylformamide, N,N-dimethylacetamide, N-methylpyrrolidin-2-one or dimethylsulfoxide. The reaction is conveniently effected at a temperature in the range, for example, 10 to 150° C. (or the boiling point of the solvent), suitably in the range 20 to 90° C.

A particularly suitable base is cesium fluoride. This reaction is suitably performed in an inert dipolar aprotic solvent such as N,N-dimethylacetamide or N,N-dimethylformamide. The reaction is suitably carried out at a temperature of from 25 to 85° C.

Process (b) By modifying a substituent in or introducing a substituent into another quinazoline derivative of Formula I or a pharmaceutically acceptable salt thereof, as hereinbefore defined except that any functional group is protected if necessary, and whereafter any protecting group that is present is removed by conventional means.

Methods for converting substituents into other substituents are known in the art. For example an alkylthio group may be oxidised to an alkylsulfinyl or alkylsulfonyl group, a cyano group reduced to an amino group, a nitro group reduced to an amino group, a hydroxy group alkylated to a methoxy group, a bromo group converted to an alkylthio group, an amino group may be acylated to give an alkanoylamino group (for example by reaction with a suitable acid chloride or acid anhydride) or an alkanoyloxy group may be hydrolysed to a hydroxy group (for example an acetyloxyacetyl group may be converted to a hydroxyacetyl group). Conveniently, one $R^1$ group may be converted into another $R^1$ group as a final step in the preparation of a compound of the Formula I.

Process (c) By reacting a compound of Formula IV:

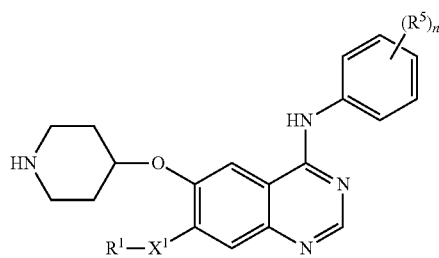

where $R^1$, $X^1$, $R^1$ and n are as defined in relation to Formula I except that any functional group is protected if necessary, with a compound of Formula V or V':

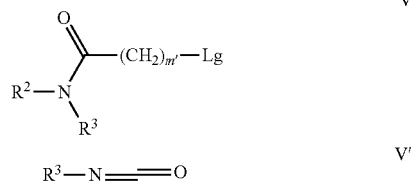

wherein $R^2$ and $R^3$ are as defined above except that any functional group is protected if necessary and m' is 0, 1, 2 or 3, provided that it is not 0 when $R^2$ is hydrogen, and Lg is a displaceable group (for example halogeno such as chloro or bromo).

The reactions described above are conveniently performed in the presence of a suitable base (such as those described above in process (a), for example potassium carbonate, triethylamine, 4-dimethylaminopyridine or di-isopropylethylamine) and conveniently in the presence of an inert solvent or diluent (for example the inert solvents and diluents described in process (a) such as N-methylpyrrolidin-2-one, acetonitrile, N,N-dimethylacetamide, methanol, ethanol or methylene chloride).

Where m' is 1, 2 or 3, the reaction is suitably effected in the presence of a source of iodide such as sodium iodide or potassium iodide, and at a temperature in the range, for example, 10 to 150° C. (or the boiling point of the solvent), suitably in the range 20 to 90° C. For example, when m is 1, the reaction may be conducted using triethylamine as a suitable base, potassium iodide as a suitable iodide source and N,N-dimethylacetamide as a suitable solvent or diluent at a temperature of about 80° C.

Where m is 0 the iodide source is not required and the typical temperature for the reaction is 0° C. to room temperature.

Reaction of the compound of Formula IV with a compound of Formula V' is useful for preparing compounds where $R^2$ is hydrogen and m is 0.

Process (d) By removal of a protecting group from a quinazoline derivative of Formula I, or a pharmaceutically acceptable salt thereof.

Suitable methods for removal of protecting groups are well known and are discussed herein. For example for the production of those compounds of the Formula I wherein $R^1$ contains a primary or secondary amino group, the cleavage of the corresponding compound of Formula I wherein $R^1$ contains a protected primary or secondary amino group.

Suitable protecting groups for an amino group are, for example, any of the protecting groups disclosed hereinbefore for an amino group. Suitable methods for the cleavage of such amino protecting groups are also disclosed hereinbefore. In particular, a suitable protecting group is a lower alkoxycarbonyl group such as a tert-butoxycarbonyl group which may be cleaved under conventional reaction conditions such as under acid-catalysed hydrolysis, for example in the presence of trifluoroacetic acid.

Process (e) By reacting a compound of the Formula II as hereinbefore defined with a compound of the Formula III as defined hereinbefore except Lg is OH under Mitsunobu conditions, and whereafter any protecting group that is present is removed by conventional means.

Suitable Mitsunobu conditions include, for example, reaction in the presence of a suitable tertiary phosphine and a di-alkylazodicarboxylate in an organic solvent such as THF, or suitably dichloromethane and in the temperature range 0° C. to 60° C., but suitably at ambient temperature. A suitable tertiary phosphine includes for example tri-n-butylphosphine or suitably tri-phenylphosphine. A suitable di-alkylazodicarboxylate includes for example diethyl azodicarboxylate (DEAD) or suitably di-tert-butyl azodicarboxylate. Details of Mitsunobu reactions are contained in Tet. Letts., 31, 699, (1990); The Mitsunobu Reaction, D. L. Hughes, Organic Reactions, 1992, Vol. 42, 335-656 and Progress in the Mitsunobu Reaction, D. L. Hughes, Organic Preparations and Procedures International, 1996, Vol. 28, 127-164.

Process (f) For the preparation of those compounds of the Formula I wherein $R^1$—$X^1$ is a hydroxy group by the cleavage of a quinazoline derivative of the Formula I wherein $R^1$—$X^1$ is a (1-6C)alkoxy group.

The cleavage reaction may conveniently be carried out by any of the many procedures known for such a transformation. The cleavage reaction of a compound of the Formula I wherein $R^1$ is a (1-6C)alkoxy group may be carried out, for example, by treatment of the quinazoline derivative with an alkali metal (1-6C)alkylsulfide such as sodium ethanethiolate or, for example, by treatment with an alkali metal diarylphosphide such as lithium diphenylphosphide. Alternatively the cleavage reaction may conveniently be carried out, for example, by treatment of the quinazoline derivative with a boron or aluminium trihalide such as boron tribromide, or by reaction with an organic or inorganic acid, for example trifluoroacetic acid. Such reactions are suitably carried out in the presence of a suitable inert solvent or diluent as defined hereinbefore. A preferred cleavage reaction is the treatment of a quinazoline derivative of the Formula I with pyridine hydrochloride. The cleavage reactions are suitably carried out at a temperature in the range, for example, from 10 to 150° C., for example from 25 to 80° C.

Process (g) For the preparation of those compounds of the Formula I wherein $X^1$ is O and $R^1$ is not hydrogen, by the reaction of a compound of the Formula VI:

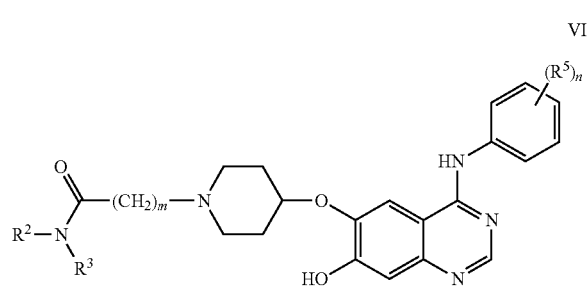

VI wherein $R^2$, $R^3$, $R^5$, m and n have any of the meanings defined hereinbefore except that any functional group is protected if necessary, with a compound of the formula $R^1$-Lg, wherein $R^1$ has any of the meanings defined hereinbefore except that it is not hydrogen and except that any functional group is protected if necessary and Lg is a displaceable group, wherein the reaction is conveniently performed in the presence of a suitable base;

and whereafter any protecting group that is present is removed by conventional means.

Suitable displaceable groups, Lg, are as hereinbefore defined for process (a), for example chloro or bromo. The reaction is suitably performed in the presence of a suitable base. Suitable solvents, diluents and bases include, for example those hereinbefore described in relation to process (a). Alternatively, Lg is a hydroxy group, whereupon the reaction can be effected under Mitsunobu conditions, as described above in relation to process (e).

Process (h) For the preparation of those compounds of the Formula I wherein $R^1$ contains a (1-6C)alkoxy or substituted (1-6C)alkoxy group or a (1-6C)alkylamino or substituted (1-6C)alkylamino group, the alkylation, conveniently in the presence of a suitable base as defined hereinbefore for process (a), of a quinazoline derivative of the Formula I wherein $R^1$ contains a hydroxy group or a primary or secondary amino group as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1-6C)alkyl chloride, bromide or iodide or a substituted (1-6C)alkyl chloride, bromide or iodide, conveniently in the presence of a suitable base as defined hereinbefore, in a suitable inert solvent or diluent as defined hereinbefore and at a temperature in the range, for example, 10 to 140° C., conveniently at or near ambient temperature. An analogous procedure may be used to introduce optionally substituted (2-6C)alkanoyloxy, (2-6C)alkanoylamino and (1-6C)alkanesulfonylamino groups into $R^1$.

Conveniently for the production of those compounds of the Formula I wherein contains a (1-6C)alkylamino or substituted (1-6C)alkylamino group, a reductive amination reaction may be employed using formaldehyde or a (2-6C)alkanolaldehyde (for example acetaldehyde or propionaldehyde). For example, for the production of those compounds of the Formula I wherein $R^1$ contains an N-methyl group, the corresponding compound containing a N—H group may be reacted with formaldehyde in the presence of a suitable reducing agent. A suitable reducing agent is, for example, a hydride reducing agent, for example formic acid, an alkali metal aluminium hydride such as lithium aluminium hydride, or, suitably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. When the reducing agent is formic acid the reaction is conveniently carried out using an aqueous solution of the formic acid. The reaction is performed at a temperature in the range, for example, 10 to 100° C., such as 70 to 90° C. or, conveniently, at or near ambient temperature. Conveniently, when the reducing agent is formic acid, protecting groups such as tert-butoxycarbonyl on the NH group to be alkylated (for example present from the synthesis of the starting material) may be removed in-situ during the reaction.

Process (i) For the preparation of those compounds of the Formula I wherein $R^1$ is substituted by a group T, wherein T is selected from (1-6C)alkylamino, di-[(1-6C)alkyl]amino, (2-6C)alkanoylamino, (1-6C)alkylthio, (1-6C)alkylsulfinyl and (1-6C)alkylsulfonyl, the reaction of a compound of the Formula VII:

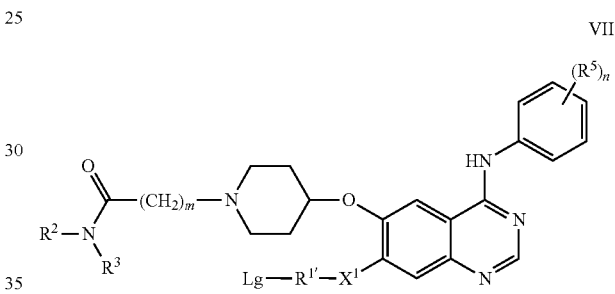

VII wherein $R^2$, $R^3$, $R^5$, $X^1$, n and m have any of the meanings defined hereinbefore except that any functional group is protected if necessary, $R^{1'}$ is a group $R^1$ as defined herein except that any T groups are replaced with Lg, and Lg is a displaceable group (for example chloro or bromo, or mesylate) with a compound of the formula TH, wherein T is as defined above except that any functional group is protected if necessary;

and whereafter any protecting group that is present is removed by conventional means.

The reaction is conveniently carried out in the presence of a suitable base. The reaction may conveniently be performed in a suitable inert solvent or diluent. Suitable bases, solvents and diluents are for example those described under process (a). The reaction is suitably performed at a temperature of for example, from 10 to 150° C., for example 30 to 60° C.

Process (j) By reacting a compound of the Formula VIII:

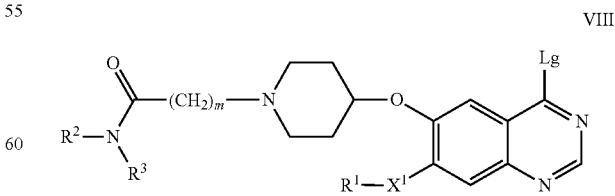

VIII wherein $R^1$, $R^2$, $R^3$, $X^1$, and m have any of the meanings defined hereinbefore except that any functional group is protected if necessary and Lg is a displaceable group as hereinbefore defined, with an aniline of the Formula IX:

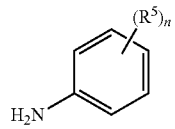

wherein $R^5$ and n have any of the meanings defined hereinbefore except that any functional group is protected if necessary, and wherein the reaction is conveniently performed in the presence of a suitable acid, and whereafter any protecting group that is present is removed by conventional means.

Suitable displaceable groups represented by Lg are as hereinbefore defined, in particular halogeno such as chloro.

The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one acetonitrile or dimethylsulfoxide. The reaction is conveniently carried out at a temperature in the range, for example, 10 to 250° C., conveniently in the range 40 to 120° C. or where a solvent or diluent is used at the reflux temperature. Conveniently, the compound of Formula VIII is reacted with a compound of the Formula IX in the presence of a protic solvent such as isopropanol, conveniently in the presence of an acid, for example a catalytic amount of an acid, under the conditions described above. Suitable acids include hydrogen chloride gas in diethyl ether or dioxane, and hydrochloric acid, for example a 4M solution of hydrogen chloride in dioxane. Alternatively, this reaction may be conveniently carried out in an aprotic solvent, such as dioxane or a dipolar aprotic solvent such as N,N-dimethylacetamide or acetonitrile in the presence of an acid, for example hydrogen chloride gas in diethyl ether or dioxane, or hydrochloric acid.

The compound of the Formula VIII, wherein Lg is halogen, may be reacted with a compound of the Formula IX in the absence of an acid. In this reaction displacement of the halogeno leaving group Lg results in the formation of the acid HLg in-situ and auto-catalysis of the reaction. Conveniently the reaction is carried out in a suitable inert organic solvent, for example isopropanol, dioxane or N,N-dimethylacetamide. Suitable conditions for this reaction are as described above.

Alternatively, the compound of Formula VIII may be reacted with a compound of the Formula IX in the presence of a suitable base. Suitable bases for this reaction are as hereinbefore defined under process (a). For example, suitable bases are alkaline earth metal amides, such as sodium bis(trimethylsilyl)amide. This reaction is conveniently performed in an inert solvent or diluent, for example those mentioned above in relation to this process (j);

Process (k) For the preparation of those compounds of the Formula I wherein m is 1, 2 or 3, the coupling of a compound of Formula X:

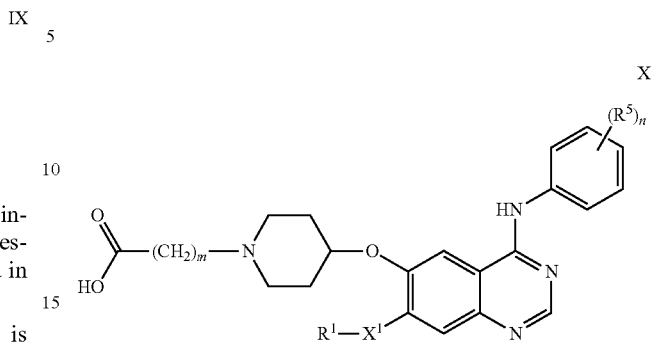

where m is 1, 2 or 3 and $R^1$, $X^1$, $R^5$ and n are as hereinbefore defined, except any functional group is protected if necessary, with a primary or secondary amine of the formula $R^2NHR^3$ where $R^2$ and $R^3$ are as defined hereinbefore; and whereafter any protecting group that is present is removed by conventional means.

The coupling reaction is conveniently carried out in the presence of a suitable coupling agent, such as a carbodiimide (for example 1-[3-(dimethylamino)propyl]-3-ethylcarbodiimide), or a suitable peptide coupling agent, for example O-(7-azabenzotriazol-1-yl)-N,N,N',N'-tetramethyluronium hexafluoro-phosphate (HATU). The reaction may also be carried out in the presence of 1-hydroxybenzotriazole in conjunction with a suitable coupling agent, such as a carbodiimide. The coupling reaction is conveniently carried out in an inert solvent such as, for example, a halogenated solvent such as methylene chloride, or a dipolar aprotic solvent such as N,N-dimethylformamide, N,N-dimethylacetamide or 1-methyl-2-pyrrolidinone. Suitably the coupling reaction is carried out in the presence of a suitable base, such as an organic amine, for example di-isopropylethylamine or 4-dimethylaminopyridine. The coupling reaction is suitably performed at −25° C. to 150° C., conveniently at ambient temperature.

Process (l) By reacting a compound of Formula IV as defined above except that any functional group is protected if necessary, with a compound of the Formula V''':

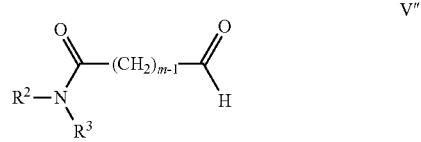

using a reductive amination procedure. Suitable reaction conditions would be apparent to the skilled person and/or from the literature.

Process (m) For compounds of the Formula I wherein $R^3$ is (2-6C)alkyl substituted on a carbon atom by an amino, (1-6C)alkylamino, di-(1-6C)alkylamino or a saturated 5 or 6 membered heterocyclic ring which contains $NR^8$ where $R^8$ is as defined in relation to Formula I, by reacting a compound of the Formula XX:

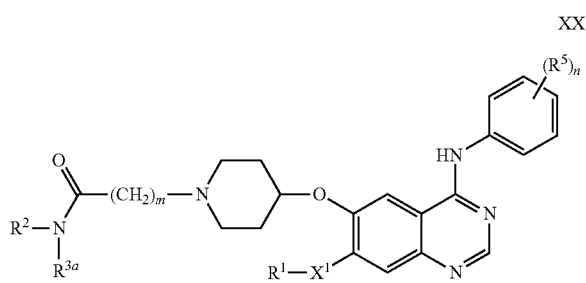

XX wherein $R^{3a}$ is Lg-(2-6C)alkyl, wherein Lg is a displaceable group as hereinbefore defined, and wherein $R^1, R^2, X^1, R^5$, m and n have any of the meanings defined hereinbefore except that any functional group is protected if necessary, with ammonia or with a suitable primary or secondary amine, such as pyrrolidine, and whereafter any protecting group that is present is removed by conventional means.

The reaction of process (m) is conveniently carried out in the presence of an inert solvent or diluent (for example the inert solvents and diluents described in processes (a) and (c), such as acetonitrile, N,N-dimethylacetamide, methanol, ethanol or methylene chloride). The reaction is suitably effected in the presence of a source of iodide such as sodium iodide or potassium iodide and at a temperature in the range, for example, 10 to 150° C. (or the boiling point of the solvent), suitably in the range 20 to 90° C.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

When a pharmaceutically-acceptable salt of a quinazoline derivative of the Formula I is required, for example an acid-addition salt, it may be obtained by, for example, reaction of said quinazoline derivative with a suitable acid using a conventional procedure. To facilitate isolation of the compound during preparation, the compound may be prepared in the form of a salt that is not a pharmaceutically acceptable salt. The resulting salt can then be modified by conventional techniques to give a pharmaceutically acceptable salt of the compound. Such techniques include, for example ion exchange techniques or re-precipitation of the compound in the presence of a pharmaceutically acceptable counter ion. For example re-precipitation in the presence of a suitable acid such as HCl to give a hydrochloride acid addition salt.

In the section above the expression "inert solvent" refers to a solvent which does not react with the starting materials, reagents, intermediates or products in a manner which adversely affects the yield of the desired product.

Preparation of Starting Materials

Compounds of Formula II are commercially available or may be prepared using conventional techniques or analogous processes to those described in the prior art. In particular those patents and applications listed hereinbefore, such as WO 96/15118, WO 01/66099 and EP 566 226. For example, the compounds of Formula II may be prepared in accordance with Reaction Scheme 1:

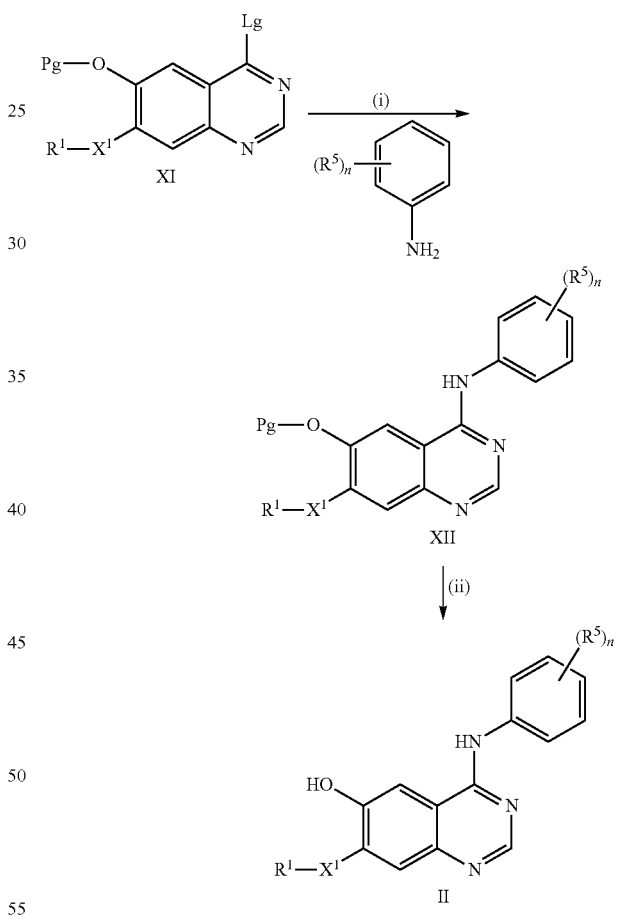

Reaction Scheme 1 wherein $R^1, X^1, R^5$, Lg and n are as hereinbefore defined and Pg is a hydroxy protecting group.

(i) Reaction suitably in an inert protic solvent (such as an alkanol for example iso-propanol), an aprotic solvent (such as dioxane) or a dipolar aprotic solvent (such as N,N-dimethylacetamide) in the presence of an acid, for example hydrogen chloride gas in diethyl ether or dioxane; or hydrochloric acid, under analogous conditions to those described above under process (j).

Alternatively the reaction may be carried out in one of the above inert solvents conveniently in the presence of a base, for example potassium carbonate. The above reactions are conveniently carried out at a temperature in the range, for example, 0 to 150° C., suitably at or near the reflux temperature of the reaction solvent.

(ii) Cleavage of Pg may be performed under standard conditions for such reactions. For example when Pg is an alkanoyl group such as acetyl, it may be cleaved by heating in the presence of a methanolic ammonia solution.

Compounds of Formula XI are known or can be prepared using known processes for the preparation of analogous compounds. If not commercially available, compounds of the Formula XI may be prepared by procedures which are selected from standard chemical techniques, techniques which are analogous to the synthesis of known, structurally similar compounds, or techniques which are analogous to the procedures described in the Examples. For example, standard chemical techniques are as described in Houben Weyl. By way of example the compound of the Formula XI in which $R^1$—$X^1$— is methoxy, Lg is chloro and Pg is acetyl may be prepared using the process illustrated in Reaction Scheme 2:

an alkanesulfonyloxy group, such as methanesulfonyloxy and Pg may be tert-butylcarboxylate.

The reaction of the compound of Formula II with the compound of Formula XVa may be carried out using analogous conditions to those described in process (a) above, followed by removal of the protecting group under standard conditions. For example, the reaction may be carried out using potassium carbonate as a suitable base, N-methylpyrrolidin-2-one as a suitable diluent and at a temperature of about 105° C.

The reaction of the compound of Formula II with the compound of Formula XVb may be carried out under Mitsunobu conditions as described in process (e) above, followed by removal of the protecting group under standard conditions.

Compounds of the Formula IV may also be prepared by reaction of a compound of the Formula IX with a compound of the Formula XVc:

Reaction Scheme 2

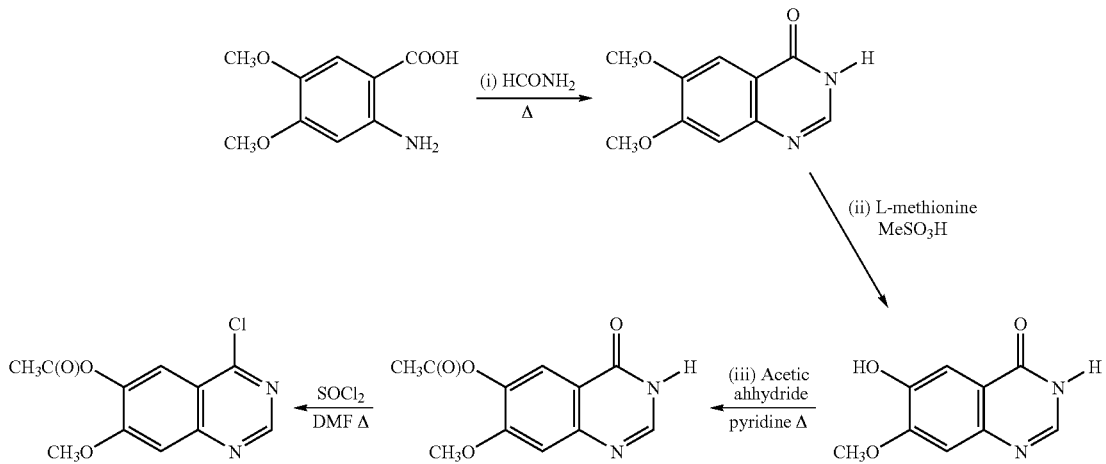

Reaction Scheme 2 may be generalised by the skilled man to apply to compounds within the present specification which are not specifically illustrated (for example to introduce a substituent other than methoxy at the 7-position in the quinazoline ring).

Compounds of the Formula III are commercially available or may be prepared using standard techniques, for example as illustrated in U.S. Pat. No. 5,252,586 and WO 94/27965.

Compounds of the Formula IV may be prepared by reaction of a compound of Formula II with a compound of XVa or XVb:

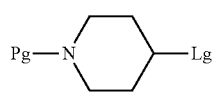

XVa

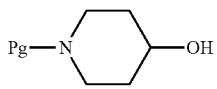

XVb wherein Lg is a displaceable group as hereinbefore defined and Pg is a suitable protecting group. For example, Lg may be

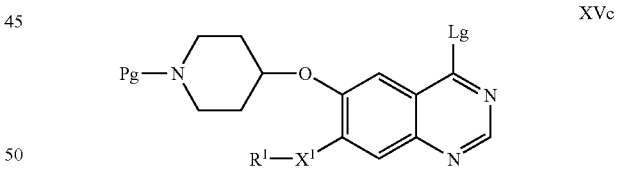

XVc wherein Lg, $X^1$ and $R^1$ are as hereinbefore defined and Pg is a suitable protecting group.

The reaction of the compound of Formula IX with the compound of Formula XVc may be carried out using analogous conditions to those described in process (j) above, followed by removal of the protecting group under standard conditions.

Compounds of the Formula VI may be prepared using process (a) or process (e) above, starting with a compound prepared, for example using reaction scheme 1.

Compounds of the Formula VII may be prepared using; for example, process (a) or process (d) or process (e) in which the group represented by $R^1$ is appropriately functionalised with a suitable displaceable group Lg such as chloro or bromo.

Compounds of the Formula VIII may be prepared using conventional methods well known in the art. For example the hydroxy protecting group, Pg, in a compound of the Formula XI as hereinbefore described in Reaction Scheme 1 is removed to give the compound of the Formula XIII:

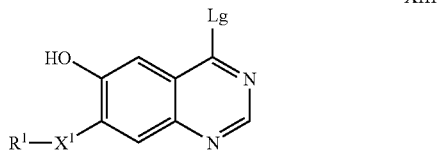

The protecting group Pg may be removed from the compound of Formula XI using conventional techniques.

The compound of the Formula XIII may then be coupled with a compound of the Formula III as hereinbefore defined using analogous conditions to those described in process (a) or process (e).

Compounds of the Formula XX may be prepared, for example, using process (a), process (c) or process (k) above.

Compounds of the Formula V, V' and IX are commercially available or may be prepared using standard techniques. Compounds of the Formula V" may be prepared using standard techniques, for example as illustrated in Synthesis, 1993, 12, 1233 and Tetrahedron, 1992, 48, 5557.

Compounds of the Formula X where m is 1, 2 or 3 may, for example, be prepared from a compound of the Formula IV by alkylation with $R^1O_2C(CH_2)_m$-Lg, wherein Lg and $R^1$ are as hereinbefore defined, in the presence of a base and using analogous conditions to those described in process (c) above, followed by transformation of the ester to the carboxylic acid (for example by saponification or acidic deprotection).

Alternatively, compounds of the Formula X where m is 1, 2 or 3 may be prepared from a compound of the Formula IV by a Mitsunobu reaction with $R^1O_2C(CH_2)_m$—OH using analogous conditions to those described in process (e) above, followed by transformation of the ester to the carboxylic acid (for example by saponification or acidic deprotection).

Certain novel intermediates utilised in the above processes are provided as a further feature of the present invention together with the process for their preparation.

According to a further feature of the present invention there is provided the compounds of the Formulae VI, VII, VIII, X and XX or a salt thereof, (including pharmaceutically acceptable salts thereof), as hereinbefore defined. Examples of such compounds are 6-{[1-(N-(2-chloroethyl)carbamoyl)piperidin-4-yl]oxy}-4-(3-chloro-2-fluoroanilino)-7-methoxyquinazoline, [4-({4-(3-chloro-2-fluoroanilino)-7-methoxyquinazolin-6-yl}oxy)piperidin-1-yl]acetic acid and [4-({4-(3-chloro-2,4-difluoroanilino)-7-methoxyquinazolin-6-yl}oxy)piperidin-1-yl]acetic acid.

Biological Assays

The inhibitory activities of compounds were assessed in non-cell based protein tyrosine kinase assays as well as in cell based proliferation assays before their in vivo activity was assessed in Xenograft studies.

a) Protein Tyrosine Kinase Phosphorylation Assays

This test measures the ability of a test compound to inhibit the phosphorylation of a tyrosine containing polypeptide substrate by EGFR or ErbB2 tyrosine kinase enzyme.

Recombinant intracellular fragments of EGFR, erbB2 and erbB4 (accession numbers X00588, X03363 and L07868 respectively) were cloned and expressed in the baculovirus/Sf21 system. Lysates were prepared from these cells by treatment with ice-cold lysis buffer (20 mM N-2-hydroxyethylpiperizine-N'-2-ethanesulfonic acid (HEPES) pH7.5, 150 mM NaCl, 10% glycerol, 1% Triton X-100, 1.5 mM $MgCl_2$, 1 mM ethylene glycol-bis(β-aminoethyl ether) N',N',N',N'-tetraacetic acid (EGTA), plus protease inhibitors and then cleared by centrifugation.

Constitutive kinase activity of the recombinant protein was determined by its ability to phosphorylate a synthetic peptide (made up of a random co-polymer of Glutamic Acid, Alanine and Tyrosine in the ratio of 6:3:1). Specifically, Maxisorb™ 96-well immunoplates were coated with synthetic peptide (0.2 μg of peptide in a 100 μl phosphate buffered saline (PBS) solution and incubated at 4° C. overnight). Plates were washed in PBS-T (phosphate buffered saline with 0.5% Tween 20) then in 50 mM HEPES pH 7.4 at room temperature to remove any excess unbound synthetic peptide. EGFR, ErbB2 or ErbB4 tyrosine kinase activity was assessed by incubation in peptide coated plates for 20 minutes at 22° C. in 100 mM HEPES pH 7.4, adenosine trisphosphate (ATP) at Km concentration for the respective enzyme, 10 mM $MnCl_2$, 0.1 mM $Na_3VO_4$, 0.2 mM DL-dithiothreitol (DTT), 0.1% Triton X-100 with test compound in DMSO (final concentration of 2.5%). Reactions were terminated by the removal of the liquid components of the assay followed by washing of the plates with PBS-T.

The immobilised phospho-peptide product of the reaction was detected by immunological methods. Firstly, plates were incubated for 90 minutes at room temperature with anti-phosphotyrosine primary antibodies that were raised in the mouse (4G10 from Upstate Biotechnology). Following extensive washing, plates were treated with Horseradish Peroxidase (HRP) conjugated sheep anti-mouse secondary antibody (NXA931 from Amersham) for 60 minutes at room temperature. After further washing, HRP activity in each well of the plate was measured colorimetrically using 22'-Azino-di-[3-ethylbenzthiazoline sulfonate (6)] diammonium salt crystals (ABTS™ from Roche) as a substrate.

Quantification of colour development and thus enzyme activity was achieved by the measurement of absorbance at 405 nm on a Molecular Devices ThermoMax microplate reader. Kinase inhibition for a given compound was expressed as an $IC_{50}$ value. This was determined by calculation of the concentration of compound that was required to give 50% inhibition of phosphorylation in this assay. The range of phosphorylation was calculated from the positive (vehicle plus ATP) and negative (vehicle minus ATP) control values.

b) EGFR Driven KB Cell Proliferation Assay

This assay measures the ability of a test compound to inhibit the proliferation of KB cells (human naso-pharangeal carcinoma obtained from the American Type Culture Collection (ATCC).

KB cells (human naso-pharangeal carcinoma obtained from the ATCC were cultured in Dulbecco's modified Eagle's medium (DMEM) containing 10% foetal calf serum, 2 mM glutamine and non-essential amino acids at 37° C. in a 7.5% $CO_2$ air incubator. Cells were harvested from the stock flasks using Trypsin/ethylaminediaminetetraacetic acid (EDTA). Cell density was measured using a haemocytometer and viability was calculated using trypan blue solution before being seeded at a density of $1.25 \times 10^3$ cells per well of a 96 well plate in DMEM containing 2.5% charcoal stripped serum, 1 mM glutamine and non-essential amino acids at 37° C. in 7.5% $CO_2$ and allowed to settle for 4 hours.

Following adhesion to the plate, the cells are treated with or without EGF (final concentration of 1 ng/ml) and with or without compound at a range of concentrations in dimethylsulfoxide (DMSO) (0.1% final) before incubation for 4 days. Following the incubation period, cell numbers were determined by addition of 50 μl of 3-(4,5-Dimethylthiazol-2-yl)-2,5-diphenyltetrazolium bromide (MTT) (stock 5 mg/ml) for 2 hours. MTT solution was then tipped off, the plate gently tapped dry and the cells dissolved upon the addition of 100 μl of DMSO.

Absorbance of the solubilised cells was read at 540 nm using a Molecular Devices ThermoMax microplate reader. Inhibition of proliferation was expressed as an $IC_{50}$ value. This was determined by calculation of the concentration of compound that was required to give 50% inhibition of proliferation. The range of proliferation was calculated from the positive (vehicle plus EGF) and negative (vehicle minus EGF) control values.

c) In Vivo Xenograft Assays (i) LOVO

This assay measures the ability of a test compound to inhibit the growth of a LoVo tumour (colorectal adenocarcinoma obtained from the ATCC) in Female Swiss athymic mice (Alderley Park, nu/nu genotype).

Female Swiss athymic (nu/nu genotype) mice were bred and maintained in Alderley Park in negative pressure Isolators (PFI Systems Ltd.). Mice were housed in a barrier facility with 12 hr light/dark cycles and provided with sterilised food and water ad libitum. All procedures were performed on mice of at least 8 weeks of age. LoVo tumour cell (colorectal adenocarcinoma obtained from the ATCC) xenografts were established in the hind flank of donor mice by sub cutaneous injections of $1\times10^7$ freshly cultured cells in 100 μl of serum free media per animal. On day 5 post-implant, mice were randomised into groups of 7 prior to the treatment with compound or vehicle control that was administered once daily at 0.1 ml/10 g body weight. Tumour volume was assessed twice weekly by bilateral Vernier calliper measurement, using the formula (length×width)×√(length×width)×(π/6), where length was the longest diameter across the tumour, and width was the corresponding perpendicular. Growth inhibition from start of study was calculated by comparison of the mean changes in tumour volume for the control and treated groups, and statistical significance between the two groups was evaluated using a Students t test.

(ii) In Vivo BT-474 Xenograft Assay

This assay measures the ability of a test compound to inhibit the growth of a BT-474 tumour cell xenograft (human mammary carcinoma obtained from Dr Baselga, Laboratorio Recerca Oncologica, Pasco Vall D'Hebron 119-129, Barcelona 08035, Spain) in Female Swiss athymic mice (Alderley Park, nu/nu genotype) (Baselga, J. et al. (1998) *Cancer Research*, 58, 2825-2831).

Female Swiss athymic (nu/nu genotype) mice were bred and maintained in Alderley Park in negative pressure Isolators (PFI Systems Ltd.). Mice were housed in a barrier facility with 12 hr light/dark cycles and provided with sterilised food and water ad libitum. All procedures were performed on mice of at least 8 weeks of age. BT-474 tumour cell xenografts were established in the hind flank of donor mice by sub-cutaneous injections of $1\times10^7$ freshly cultured cells in 100 μl of serum free media with 50% Matrigel per animal. On day 14 post-implant, mice were randomised into groups of 10 prior to the treatment with compound or vehicle control that was administered once daily at 0.1 ml/kg body weight. Tumour volume was assessed twice weekly by bilateral Vernier calliper measurement, using the formula (length×width)×√(length×width)×(π/6), where length was the longest diameter across the tumour, and width was the corresponding perpendicular. Growth inhibition from start of treatment was calculated by comparison of the mean changes in tumour volume for the control and treated groups, and statistical significance between the two groups was evaluated using a Students t test.

d) hERG-Encoded Potassium Channel Inhibition Assay

This assay determines the ability of a test compound to inhibit the tail current flowing through the human ether-a-go-go-related-gene (hERG)-encoded potassium channel.

Human embryonic kidney (HEK) cells expressing the hERG-encoded channel were grown in Minimum Essential Medium Eagle (EMEM; Sigma-Aldrich catalogue number M2279), supplemented with 10% Foetal Calf Serum (Labtech International; product number 4-101-500), 10% M1 serum-free supplement (Egg Technologies; product number 70916) and 0.4 mg/ml Geneticin G418 (Sigma-Aldrich; catalogue number G7034). One or two days before each experiment, the cells were detached from the tissue culture flasks with Accutase (TCS Biologicals) using standard tissue culture methods. They were then put onto glass coverslips resting in wells of a 12 well plate and covered with 2 ml of the growing media.

For each cell recorded, a glass coverslip containing the cells was placed at the bottom of a Perspex chamber containing bath solution (sec below) at room temperature (~20° C.). This chamber was fixed to the stage of an inverted, phase-contrast microscope. Immediately after placing the coverslip in the chamber, bath solution was perfused into the chamber from a gravity-fed reservoir for 2 minutes at a rate of ~2 ml/min. After this time, perfusion was stopped.

A patch pipette made from borosilicate glass tubing (GC120F, Harvard Apparatus) using a P-97 micropipette puller (Sutter Instrument Co.) was filled with pipette solution (see hereinafter). The pipette was connected to the headstage of the patch clamp amplifier (Axopatch 200B, Axon Instruments) via a silver/silver chloride wire. The headstage ground was connected to the earth electrode. This consisted of a silver/silver chloride wire embedded in 3% agar made up with 0.85% sodium chloride.

The cell was recorded in the whole cell configuration of the patch clamp technique. Following "break-in", which was done at a holding potential of −80 mV (set by the amplifier), and appropriate adjustment of series resistance and capacitance controls, electrophysiology software (Clampex, Axon Instruments) was used to set a holding potential (−80 mV) and to deliver a voltage protocol. This protocol was applied every 15 seconds and consisted of a 1 s step to +40 mV followed by a 1 s step to −50 mV.

The current response to each imposed voltage protocol was low pass filtered by the amplifier at 1 kHz. The filtered signal was then acquired, on line, by digitising this analogue signal from the amplifier with an analogue to digital converter. The digitised signal was then captured on a computer running Clampex software (Axon Instruments). During the holding potential and the step to +40 mV the current was sampled at 1 kHz. The sampling rate was then set to 5 kHz for the remainder of the voltage protocol.

The compositions, pH and osmolarity of the bath and pipette solution are tabulated below.

| Salt | Pipette (mM) | Bath (mM) |
|---|---|---|
| NaCl | — | 137 |
| KCl | 130 | 4 |
| $MgCl_2$ | 1 | 1 |
| $CaCl_2$ | — | 1.8 |
| HEPES | 10 | 10 |

-continued

| Salt | Pipette (mM) | Bath (mM) |
|---|---|---|
| glucose | — | 10 |
| Na$_2$ATP | 5 | — |
| EGTA | 5 | — |

| Parameter | Pipette | Bath |
|---|---|---|
| pH | 7.18-7.22 | 7.40 |
| pH adjustment with | 1M KOH | 1M NaOH |
| Osmolarity (mOsm) | 275-285 | 285-295 |

The amplitude of the hERG-encoded potassium channel tail current following the step from +40 mV to −50 mV was recorded on-line by Clampex software (Axon Instruments). Following stabilisation of the tail current amplitude, bath solution containing the vehicle for the test substance was applied to the cell. Providing the vehicle application had no significant effect on tail current amplitude, a cumulative concentration effect curve to the compound was then constructed.

The effect of each concentration of test compound was quantified by expressing the tail current amplitude in the presence of a given concentration of test compound as a percentage of that in the presence of vehicle.

Test compound potency (IC$_{50}$) was determined by fitting the percentage inhibition values making up the concentration-effect to a four parameter Hill equation using a standard data-fitting package. If the level of inhibition seen at the highest test concentration did not exceed 50%, no potency value was produced and a percentage inhibition value at that concentration was quoted.

e) Clone 24 Phospho-erbB2 Cell Assay

This immunofluorescence end point assay measures the ability of a test compound to inhibit the phosphorylation of erbB2 in a MCF7 (breast carcinoma) derived cell line which was generated by transfecting MCF7 cells with the full length erbB2 gene using standard methods to give a cell line that overexpresses full length wild type erbB2 protein (hereinafter 'Clone 24' cells).

Clone 24 cells were cultured in Growth Medium (phenol red free Dulbecco's modified Eagle's medium (DMEM) containing 10% foetal bovine serum, 2 mM glutamine and 1.2 mg/ml G418) in a 7.5% CO$_2$ air incubator at 37° C. Cells were harvested from T75 stock flasks by washing once in PBS (phosphate buffered saline, pH7.4, Gibco No. 10010-015) and harvested using 2 mls of Trypsin (1.25 mg/ml)/ethylaminediaminetetraacetic acid (EDTA) (0.8 mg/ml) solution. The cells were resuspended in Growth Medium. Cell density was measured using a haemocytometer and viability was calculated using Trypan Blue solution before being further diluted in Growth Medium and seeded at a density of 1×10$^4$ cells per well (in 100 ul) into clear bottomed 96 well plates (Packard, No. 6005182).

3 days later, Growth Medium was removed from the wells and replaced with 100 ul Assay Medium (phenol red free DMEM, 2 mM glutamine, 1.2 mg/ml G418) either with or without erbB inhibitor compound. Plates were returned to the incubator for 4 hrs and then 20 µl of 20% formaldehyde solution in PBS was added to each well and the plate was left at room temperature for 30 minutes. This fixative solution was removed with a multichannel pipette, 100 µl of PBS was added to each well and then removed with a multichannel pipette and then 50 µl PBS was added to each well. Plates were then sealed and stored for up to 2 weeks at 4° C.

Immunostaining was performed at room temperature. Wells were washed once with 200 µl PBS/Tween 20 (made by adding 1 sachet of PBS/Tween dry powder (Sigma, No. P3563) to IL of double distilled H$_2$O) using a plate washer then 200 µl Blocking Solution (5% Marvel dried skimmed milk (Nestle) in PBS/Tween 20) was added and incubated for 10 minutes. Blocking Solution was removed using a plate washer and 200 µl of 0.5% Triton X-100/PBS was added to permeabalise the cells. After 10 minutes, the plate was washed with 200 µl PBS/Tween 20 and then 200 µl Blocking Solution was added once again and incubated for 15 minutes. Following removal of the Blocking Solution with a plate washer, 30 µl of rabbit polyclonal anti-phospho ErbB2 IgG antibody (epitope phospho-Tyr 1248, SantaCruz, No. SC-12352-R), diluted 1:250 in Blocking Solution, was added to each well and incubated for 2 hours. Then this primary antibody solution was removed from the wells using a plate washer followed by two 200 µl PBS/Tween 20 washes using a plate washer. Then 30 µl of Alexa-Fluor 488 goat anti-rabbit IgG secondary antibody (Molecular Probes, No. A-11008), diluted 1:750 in Blocking Solution, was added to each well. From now onwards, wherever possible, plates were protected from light exposure, at this stage by sealing with black backing tape. The plates were incubated for 45 minutes and then the secondary antibody solution was removed from the wells followed by two 200 µl PBS/Tween 20 washes using a plate washer. Then 100 µl PBS was added to each plate, incubated for 10 minutes and then removed using a plate washer. Then a further 100 µl PBS was added to each plate and then, without prolonged incubation, removed using a plate washer. Then 50 µl of PBS was added to each well and plates were resealed with black backing tape and stored for up to 2 days at 4° C. before analysis.

The Fluorescence signal is each well was measured using an Acumen Explorer Instrument (Acumen Bioscience Ltd.), a plate reader that can be used to rapidly quantitate features of images generated by laser-scanning. The instrument was set to measure the number of fluorescent objects above a pre-set threshold value and this provided a measure of the phosphorylation status of erbB2 protein. Fluorescence dose response data obtained with each compound was exported into a suitable software package (such as Origin) to perform curve fitting analysis. Inhibition of erbB2 phosphorylation was expressed as an IC$_{50}$ value. This was determined by calculation of the concentration of compound that was required to give 50% inhibition of erbB2 phosphorylation signal.

Although the pharmacological properties of the compounds of the Formula I vary with structural change as expected, in general activity possessed by compounds of the Formula may be demonstrated at the following concentrations or doses in one or more of the above tests:—

Test (a):—IC$_{50}$ in the range, for example, 0.001-10 µM;
Test (b):—IC$_{50}$ in the range, for example, 0.001-10 µM;
Test (e):—IC$_{50}$ in the range, for example, 0.001-10 µM;
Test (c):—activity in the range, for example, 1-200 mg/kg/day;

By way of example, Table A illustrates the activity of representative compounds according to the invention. Column 2 of Table A shows IC$_{50}$ data from Test (a) for the inhibition of EGFR tyrosine kinase protein phosphorylation; column 3 shows IC$_{50}$ data from Test (a) for the inhibition of erbB2 tyrosine kinase protein phosphorylation; column 4 shows IC$_{50}$ data for inhibition of proliferation of KB cells in Test (b) described above; and column 5 shows IC$_{50}$ data for inhibition of phosphorylation of erbB2 in a MCF7 derived cell line in Test (e) described above:

TABLE A

| Example Number | IC$_{50}$ (µM) Test (a): Inhibition of EGFR tyrosine kinase protein phosphorylation | IC$_{50}$ (µM) Test (a): Inhibition of erbB2 tyrosine kinase protein phosphorylation | IC$_{50}$ (µM) Test (b): EGFR driven KB cell proliferation assay | IC$_{50}$ (µM) Test (e): Inhibition of erbB2 tyrosine kinase protein phosphorylation |
|---|---|---|---|---|
| 5 | 0.004 | 0.047 | 0.009 | 0.006 |
| 7 | 0.003 | 0.013 | 0.017 | 0.014 |
| 10 | 0.004 | 0.010 | — | 0.013 |

According to a further aspect of the invention there is provided a pharmaceutical composition which comprises a quinazoline derivative of the Formula I, or a pharmaceutically-acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

We have found that the compounds of the present invention possess anti-proliferative properties such as anti-cancer properties that are believed to arise from their erbB family receptor tyrosine kinase inhibitory activity, and particularly a mixed erbB2/EGF profile.

Accordingly, the compounds of the present invention are expected to be useful in the treatment of diseases or medical conditions mediated alone or in part by erbB receptor tyrosine kinases, i.e. the compounds may be used to produce an erbB receptor tyrosine kinase inhibitory effect in a warm-blooded animal in need of such treatment. Thus the compounds of the present invention provide a method for the treatment of malignant cells characterised by inhibition of one or more of the erbB family of receptor tyrosine kinases. Particularly the compounds of the invention may be used to produce an anti-proliferative and/or pro-apoptotic and/or anti-invasive effect mediated alone or in part by the inhibition of erbB receptor tyrosine kinases. Particularly, the compounds of the present invention are expected to be useful in the prevention or treatment of those tumours that are sensitive to inhibition of one or more of the erbB receptor tyrosine kinases, that are involved in the signal transduction steps which drive proliferation and survival of these tumour cells. Accordingly the compounds of the present invention are expected to be useful in the treatment of psoriasis, benign prostatic hyperplasia (BPH), atherosclerosis and restenosis and/or cancer by providing an anti-proliferative effect, particularly in the treatment of erbB receptor tyrosine kinase sensitive cancers. Such benign or malignant tumours may affect any tissue and include non-solid tumours such as leukaemia, multiple myeloma or lymphoma, and also solid tumours, for example bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancers.

According to this aspect of the invention there is provided a compound of the Formula I, or a pharmaceutically acceptable salt thereof, for use as a medicament.

According to a further aspect of the invention there is provided a compound of the Formula I, or a pharmaceutically acceptable salt thereof, for use in the production of an anti-proliferative effect in a warm-blooded animal such as man.

Thus according to this aspect of the invention there is provided the use of a quinazoline derivative of the Formula I, or a pharmaceutically-acceptable salt thereof, as defined hereinbefore in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of a quinazoline derivative of the Formula I, or a pharmaceutically acceptable salt thereof, as hereinbefore defined.

According to a further aspect of the invention there is provided the use of a quinazoline derivative of the Formula I, or a pharmaceutically-acceptable salt thereof, as defined hereinbefore in the manufacture of a medicament for use in the prevention or treatment of those tumours which are sensitive to inhibition of erbB receptor tyrosine kinases, such as a combination of EGFR and erbB2, that are involved in the signal transduction steps which lead to the proliferation of tumour cells.

According to a further feature of this aspect of the invention there is provided a method for the prevention or treatment of those tumours which are sensitive to inhibition of one or more of the erbB family of receptor tyrosine kinases, such as a combination of EGFR and erbB2, that are involved in the signal transduction steps which lead to the proliferation and/or survival of tumour cells which comprises administering to said animal an effective amount of a quinazoline derivative of the Formula I, or a pharmaceutically-acceptable salt thereof, as defined hereinbefore.

According to a further feature of this aspect of the invention there is provided a compound of the Formula I, or a pharmaceutically acceptable salt thereof, for use in the prevention or treatment of those tumours which are sensitive to inhibition of erbB receptor tyrosine kinases, such as a combination of EGFR and erbB2, that are involved in the signal transduction steps which lead to the proliferation of tumour cells.

According to a further aspect of the invention there is provided the use of a quinazoline derivative of the Formula I, or a pharmaceutically-acceptable salt thereof, as defined hereinbefore in the manufacture of a medicament for use in providing a combined EGFR and erbB2 tyrosine kinase inhibitory effect.

According to a further feature of this aspect of the invention there is provided a method for providing a combined EGFR and erbB2 tyrosine kinase inhibitory effect which comprises administering to said animal an effective amount of a quinazoline derivative of the Formula I, or a pharmaceutically-acceptable salt thereof, as defined hereinbefore.

According to a further feature of this aspect of the invention there is provided a compound of the Formula I, or a pharmaceutically acceptable salt thereof, for use in providing a combined EGFR and erbB2 tyrosine kinase inhibitory effect.

According to a further aspect of the present invention there is provided the use of a quinazoline derivative of the Formula I, or a pharmaceutically-acceptable salt thereof, as defined hereinbefore in the manufacture of a medicament for use in the treatment of a cancer (for example a cancer selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer).

According to a further feature of this aspect of the invention there is provided a method for treating a cancer (for example a cancer selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer) in a warm-blooded animal, such as man, in need of such treatment, which comprises administering to said animal an effective amount of a quinazoline derivative of the Formula I, or a pharmaceutically-acceptable salt thereof, as defined hereinbefore.

According to a further aspect of the invention there is provided a compound of the Formula I, or a pharmaceutically acceptable salt thereof, for use in the treatment of a cancer (for example selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer).

As mentioned above the size of the dose required for the therapeutic or prophlyactic treatment of a particular disease will necessarily be varied depending upon, amongst other things, the host treated, the route of administration and the severity of the illness being treated.

The anti-proliferative treatment defined hereinbefore may be applied as a sole therapy or may involve, in addition to the quinazoline derivative of the invention, conventional surgery or radiotherapy or chemotherapy. Such chemotherapy may include one or more of the following categories of anti-tumour agents:—

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example other inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy) quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinazoline derivative of the Formula I as defined hereinbefore and an additional anti-tumour agent as defined hereinbefore for the conjoint treatment of cancer.

Although the compounds of the Formula I are primarily of value as therapeutic agents for use in warm-blooded animals (including man), they are also useful whenever it is required to inhibit the effects of the erbB receptor tyrosine protein kinases. Thus, they are useful as pharmacological standards for use in the development of new biological tests and in the search for new pharmacological agents.

The invention will now be illustrated by the following non-limiting examples in which, unless stated otherwise:
(i) temperatures are given in degrees Celsius (° C.); operations were carried out at room or ambient temperature, that is, at a temperature in the range of 18-25° C.;
(ii) organic solutions were dried over anhydrous magnesium sulfate; evaporation of solvent was carried out using a rotary evaporator under reduced pressure (600-4000 Pascals; 4.5-30 mmHg) with a bath temperature of up to 60° C.;
(iii) chromatography means flash chromatography on silica gel; thin layer chromatography (TLC) was carried out on silica gel plates;
(iv) in general, the course of reactions was followed by TLC and/or analytical LCMS, and reaction times are given for illustration only;
(v) final products had satisfactory proton nuclear magnetic resonance (NMR) spectra and/or mass spectral data;
(vi) yields are given for illustration only and are not necessarily those which can be obtained by diligent process development; preparations were repeated if more material was required;
(vii) when given, NMR data is in the form of delta values for major diagnostic protons, given in parts per million (ppm) relative to tetramethylsilane (TMS) as an internal standard, determined at 400 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; b, broad;
(viii) chemical symbols have their usual meanings; SI units and symbols are used;
(ix) solvent ratios are given in volume:volume (v/v) terms; and
(x) mass spectra (MS) were run with an electron energy of 70 electron volts in the chemical ionization (CI) mode using a direct exposure probe and ionization was effected by electrospray; values for m/z are given; generally, only ions which indicate the parent mass are reported; and unless otherwise stated, the mass ion quoted is $(MH)^+$;
(xi) unless stated otherwise compounds containing an asymmetrically substituted carbon and/or sulfur atom have not been resolved;
(xii) where a synthesis is described as being analogous to that described in a previous example the amounts used are the millimolar ratio equivalents to those used in the previous example;
(xiii) the following abbreviations have been used:
DCM dichloromethane;
DMF N,N-dimethylformamide;
DMA N,N-dimethylacetamide;
THF Tetrahydrofuran;
(xiv) where a synthesis is described as leading to an acid addition salt (e.g. HCl salt), the specific stoichiometry of the salt was not confirmed.
(xv) In Examples 1 to 12 unless otherwise stated, all NMR data is reported on free-base material, with isolated salts converted to the free-base form prior to characterisation.

EXAMPLE 1

Preparation of 4-(3-Chloro-2-fluoroanilino)-7-methoxy-6-{[1-(N-methylcarbamoylmethyl)piperidin-4-yl]oxy}quinazoline 2-Chloro-N-methylacetamide (32 mg, 0.3 mmol) was added dropwise to a mixture of 4-(3-chloro-2-fluoroanilino)-7-methoxy-6-[(piperidin-4-yl)oxy]quinazoline (120 mg, 0.3 mmol), potassium iodide (16 mg, 0.1 mmol), and potassium carbonate (50 mg, 0.36 mmol) in acetonitrile (5 ml). The mixture was heated at reflux for one hour. After evaporation of the solvents under vacuum, the residue was taken up in dichloromethane. The organic solution was washed with water and brine, dried over magnesium sulfate. After evaporation of the solvents under vacuum, the residue was purified by chromatography on silica gel (eluant: 1% to 2% 7N methanolic ammonia in dichloromethane) to give the title compound as a white solid (85 mg, 60%).

$^1$H NMR Spectrum: (CDCl$_3$) 1.98 (m, 2H), 2.08 (m, 2H), 2.46 (m, 2H), 2.85 (m, 2H), 2.87 (d, 3H), 3.07 (s, 2H), 4.02 (s, 3H), 4.49 (m, 1H), 7.16 (m, 4H), 7.31 (m, 2H), 8.49 (m, 1H), 8.71 (s, 1H); Mass estrum: MH$^+$ 474

4-(3-Chloro-2-fluoroanilino)-7-methoxy-6-[(piperidin-4-yl)oxy]quinazoline used as the starting material was prepared as follows:

Step 1

6-Acetoxy-4-(3-chloro-2-fluoroanilino)-7-methoxyquinazoline hydrochloride

6-Acetoxy-4-chloro-7-methoxyquinazoline (prepared as described in Example 25-5 of in WO01/66099, 6.00 g, 23.8 mmol) and 3-chloro-2-fluoroaniline (3.46 g, 23.8 mmol)

were suspended in iso-propanol (200 ml). The mixture was heated to 80° C. under reflux for 3 hours. The solvent was evaporated; the residue was crystallised from acetonitrile, giving the product hydrochloride as a pale pink crystalline solid (8.16 g, 92%);

$^1$H NMR: 2.37 (s, 3H), 4.00 (s, 3H), 7.34 (ddd, 1H), 7.48 (s, 1H), 7.52 (ddd, 1H), 7.61 (ddd, 1H), 8.62 (s, 1H), 8.86 (s, 1H); Mass Spectrum: 362.4, 364.4.

Step 2

4-(3-Chloro-2-fluoroanilino)-6-hydroxy-7-methoxyquinazoline

6-Acetoxy-4-(3-chloro-2-fluoroanilino)-7-methoxyquinazoline hydrochloride from step 1 (8.72 g, 21.9 mmol) was dissolved in methanol (200 ml). Concentrated aqueous ammonia (15 ml) was added, and the solution heated to 50° C. with stirring for 2 hours, causing precipitation of a cream coloured solid. The solid was collected by filtration, washed with diethyl ether (3×200 ml), and dried in vacuo at 60° C. over diphosphorous pentoxide, giving the product as an off white solid (5.40 g, 77%);

$^1$H NMR: 3.95 (s, 3H), 7.19 (s, 1H), 7.23 (dd, 1H), 7.42 (dd, 1H), 7.50 (dd, 1H), 7.64 (s, 1H), 8.32 (s, 1H), 9.43 (s, 1H), 9.67 (br.s, 1H); Mass Spectrum: 320.4, 322.4.

Step 3

6-{[(1-tert-Butoxycarbonyl)piperidin-4-yl]oxy}-4-(3-chloro-2-fluoroanilino)-7-methoxy quinazoline 4-(3-Chloro-2-fluoroanilino)-6-hydroxy-7-methoxyquinazoline from Step 2 (1870 mg, 5.85 mmol) was dissolved in DMA (50 ml). tert-Butyl(4-methanesulfonyloxy) piperidine-1-carboxylate (prepared as in Chemical & Pharmaceutical Bulletin 2001, 49(7), 822-829; 490 mg, 1.76 mmol) and cesium fluoride (890 mg, 5.85 mmol) were added, and the mixture was heated to 85° C. with stirring. At intervals of 2 hours, 4 hours and 6 hours, tert-butyl 4-methanesulfonyloxypiperidine-1-carboxylate and cesium fluoride were added in the above quantities to the reaction mixture. Heating was continued at 85° C. for a further 6 hours after the final addition. The solvent was evaporated, and the residue was partitioned between DCM (150 ml) and H$_2$O (150 ml). The aqueous layer was extracted with DCM (4×100 ml), and the extractions combined with the DCM layer. The combined DCM fractions were dried over MgSO$_4$ and evaporated. The residue was purified by chromatography, eluting with 0 to 2.5% (7:1 MeOH/concentrated aqueous NH$_4$OH) in DCM. The appropriate fractions were combined and evaporated, giving the product as a light brown foam (2.40 g, 58%, allowing for 2.3 equivalents of residual DMA);

$^1$H NMR: 1.40 (s, 9H), 1.60-1.65 (m, 2H), 1.95-2.00 (m, 2H), 3.20-3.25 (m, 2H), 3.65-3.70 (m, 2H), 3.92 (s, 3H), 4.68 (m, 1H), 7.21 (s, 1H), 7.27 (dd, 1H), 7.47 (ddd, 1H), 7.51 (dd, 1H), 7.85 (s, 1H), 8.36 (s, 1H), 9.53 (s, 1H); Mass Spectrum: 503.5, 505.5.

Step 4

4-(3-chloro-2-fluoroanilino)-7-methoxy-6-[(piperidin-4-yl)oxy]quinazoline 6-({[(1-tert-Butoxycarbonyl)piperidin-4-yl]oxy)-4-(3-chloro-2-fluoroanilino)-7-methoxyquinazoline from step 3 (350 mg, 0.70 mmol) was dissolved in trifluoroacetic acid (5 ml), and the solution stood for 2 hours. The excess trifluoroacetic acid was evaporated, and the residue was azeotroped twice with DCM. The residue was purified by chromatography, eluting with 0 to 4% (7:1 MeOH/concentrated aqueous NH$_4$OH) in DCM. Evaporation of the appropriate fractions gave the product as an off-white solid (270 mg, 96%);

$^1$H NMR: 1.53-1.64 (m, 2H), 2.00-2.05 (m, 2H), 2.64-2.72 (m, 2H), 3.00-3.07 (m, 2H), 3.92 (s, 3H), 4.60 (m, 1H), 7.20 (s, 1H), 7.26 (ddd, 1H), 7.47 (dd, 1H), 7.50 (dd, 1H), 7.82 (s, 1H), 8.34 (s, 1H), 9.56 (s, 1H); Mass Spectrum: 403.2, 405.2.

EXAMPLE 2

Preparation of 4-(3-Chloro-2-fluoroanilino)-7-methoxy-6-{[1-(N-methylcarbamoyl) piperidin-4-yl]oxy}quinazoline Methylisocyanate (20.4 µl, 0.33 mmol) was added dropwise to a mixture of 4-(3-chloro-2-fluoroanilino)-7-methoxy-6-[(piperidin-4-yl)oxy]quinazoline (120 mg, 0.3 mmol) in dichloromethane (5 ml) at room temperature. The mixture was stirred at room temperature for 4 hours. After evaporation of the solvents under vacuum, the residue was purified by chromatography on silica gel (eluant: 2% 7N methanolic ammonia in dichloromethane) to give the title compound as a white solid (100 mg, 72%).

$^1$H NMR Spectrum: (CDCl$_3$) 1.98 (m, 2H), 2.08 (m, 2H), 2.83 (d, 3H), 3.32 (m, 2H), 3.72 (m, 2H), 4.01 (s, 3H), 4.48 (m, 1H), 4.64 (m, 1H), 7.16 (m, 2H), 7.23 (s, 1H), 7.31 (s, 1H), 7.38 (br s, 1H), 8.44 (m, 1H), 8.70 (s, 1H); Mass spectrum: MH$^+$ 460.

EXAMPLE 3

Preparation of 4-(3-Chloro-2-fluoroanilino)-7-methoxy-6-{[1-(N-(2-pyrrolin-1-ylethyl) carbamoyl)piperidin-4-yl]oxy}quinazoline A mixture of 6-{[1-(N-(2-chloroethyl)carbamoyl)piperidin-4-yl]oxy}-4-(3-chloro-2-fluoroanilino)-7-methoxyquinazoline (204 mg, 0.4 mmol), pyrrolidine (0.14 ml, 1.6 mmol) and potassium iodide (134 mg, 0.8 mmol) in dimethylacetamide (3 ml) was heated at 80° C. for 4 hours. After cooling and evaporation of the solvents under vacuum, the residue was partitioned in water, dichloromethane and extracted with dichloromethane. The organic layer was washed with water and brine, and dried over magnesium sulfate. After evaporation of the solvents under vacuum, the residue was purified by chromatography on silica gel (eluant: 3% to 4% 7N methanolic ammonia in dichloromethane) to give the title compound as a white solid (77 mg, 36%).

$^1$H NMR Spectrum: (CDCl$_3$) 1.78 (m, 4H), 1.93 (m, 2H), 2.04 (m, 2H), 2.53 (m, 4H), 2.62 (t, 2H), 3.33 (m, 4H), 3.75 (m, 2H), 4.01 (s, 3H), 4.64 (m, 1H), 5.27 (m, 1H), 7.16 (m, 2H), 7.22 (s, 1H), 7.30 (s, 1H), 7.36 (br s, 1H), 8.45 (m, 1H), 8.70 (s, 1H); Mass spectrum: MH$^+$ 543.

The 6-{[1-(N-(2-chloroethyl)carbamoyl)piperidin-4-yl]oxy}-4-(3-chloro-2-fluoroanilino)-7-methoxyquinazoline used as starting material was made similarly to Example 2 by reaction of 4-(3-chloro-2-fluoroanilino)-7-methoxy-6-[(piperidin-4-yl)oxy]quinazoline (160 mg, 0.4 mmol) and 2-chloroethylisocyanate (34 µl, 0.4 mmol). Yield: 200 mg, 100%. Mass spectrum: MH$^+$ 508, 510.

EXAMPLE 4

Preparation of 4-(3-Chloro-2-fluoroanilino)-7-methoxy-6-{[1-(morpholin-4-ylcarbonyl) piperidin-4-yl]oxy}quinazoline 4-Morpholinylcarbonyl chloride (35 μl, 0.3 mmol) was added dropwise to a ice-cooled mixture of 4-(3-chloro-2-fluoroanilino)-7-methoxy-6-[(piperidin-4-yl)oxy]quinazoline (120 mg, 0.3 mmol) and diisopropylethylamine (63 μl, 0.36 mmol) in dichloromethane (5 ml). At the end of the addition, the mixture was stirred at room temperature for 18 hours. The mixture was diluted with dichloromethane, washed with water and brine and dried over magnesium sulfate. After evaporation of the solvents under vacuum, the residue was purified by chromatography on silica gel (eluant: 1% to 2% 7N methanolic ammonia in dichloromethane) to give the title compound as a white solid (100 mg, 64%).

$^1$H NMR Spectrum: (CDCl$_3$) 1.93 (m, 2H), 2.05 (m, 2H), 3.20 (m, 2H), 3.29 (m, 4H), 3.62 (m, 2H), 3.70 (m, 4H), 4.01 (s, 3H), 4.64 (m, 1H), 7.16 (m, 2H), 7.20 (s, 1H), 7.31 (m, 2H), 8.49 (m, 1H), 8.71 (s, 1H); Mass spectrum: MH$^+$ 516.

EXAMPLE 5

4-(3-chloro-2,4-difluoroanilino)-7-methoxy-6-{[1-(N-methycarbamoylmethyl)piperidin-4-yl]oxy}quinazoline 2-Chloro-N-methylacetamide (51 mg, 0.47 mmol) was added dropwise to a mixture of 4-(3-chloro-2,4-difluoroanilino)-7-methoxy-6-[(piperidin-4-yl)oxy]quinazoline (200 mg, 0.47 mmol), potassium iodide (79 mg, 0.47 mmol) and potassium carbonate (79 mg, 0.57 mmol) in dimethylacetamide (5 ml). The mixture was heated at 70° C. for one hour. After cooling and filtration of the solids, the filtrate was purified on an HPLC column (C18, 5 microns, 19 mm diameter, 100 mm length) of a preparative HPLC-MS system eluting with a mixture of water and acetonitrile containing 2 g/l of ammonium formate (gradient) to give the title compound (55 mg, 24%) as a white solid.

$^1$H NMR Spectrum: (CDCl$_3$) 1.98 (m, 2H), 2.07 (m, 2H), 2.44 (m, 2H), 2.86 (m, 2H), 2.87 (d, 3H), 3.06 (s, 2H), 4.01 (s, 3H), 4.48 (m, 1H), 7.07 (m, 1H), 7.15 (m, 1H), 7.20 (s, 1H), 7.30 (m, 2H), 8.32 (m, 1H), 8.66 (s, 1H); Mass spectrum: MH$^+$ 492.

4-(3-chloro-2,4-difluoroanilino)-7-methoxy-6-[(piperidin-4-yl)oxy]quinazoline used as starting material was made as follows:

3-Chloro-2,4-difluoroaniline (1.7 g, 10.1 mmol) and 5N hydrogen chloride in isopropanol (2 ml) were added to a suspension of tert-butyl 4-[(4-chloro-7-methoxyquinazolin-6-yl)oxy]piperidine-1-carboxylate (4 g, 10.1 mmol, PCT Int. Appl. WO2003082831, AstraZeneca) in isopropanol (50 ml). The mixture was stirred at 80° C. for 3 hours. After evaporation of the solvents, the residue was purified by chromatography on silica gel (eluant: 5-10% 7N methanolic ammonia in dichloromethane) to give 4-(3-chloro-2,4-difluoroanilino)-7-methoxy-6-[(piperidin-4-yl)oxy]quinazoline (3.63 g, 85%) as a white solid.

$^1$H NMR Spectrum: (CDCl$_3$+CD$_3$CO$_2$D): 2.15 (m, 2H), 2.30 (m, 2H), 3.34 (m, 2H), 3.47 (m, 2H), 4.01 (s, 3H), 4.91 (m, 1H), 7.03 (m, 1H), 7.58 (m, 2H), 7.90 (s, 1H), 8.55 (s, 1H); Mass Spectrum: MH$^+$ 421.

EXAMPLES 6 to 10

A suspension of [4-({4-(3-chloro-2-fluoroanilino)-7-methoxyquinazolin-6-yl}oxy)piperidin-1-yl]acetic acid dihydrochloride salt (212 mg, 0.4 mmol), 1-hydroxybenzotriazole (66 mg, 0.48 mmol), diisopropylethylamine (0.14 ml, 0.8 mmol), the appropriate amine (0.48 mmol) and 1-(3-dimethylaminopropyl)-3-ethylcarbodiimide hydrochloride (92 mg, 0.48 mmol) in dichloromethane (5 ml) was stirred for 2 hours. The mixture was washed with water, 10% aqueous sodium bicarbonate and brine and dried over magnesium sulfate. After evaporation of the solvents, the residue was purified by chromatography on silica gel (eluant: 2-3% 7N methanolic ammonia in dichloromethane) and triturated in acetonitrile to give the title compound.

EXAMPLE 6

4-(3-chloro-2-fluoroanilino)-6-{[1-(N-ethylcarbamoylmethyl)piperidin-4-yl]oxy}-7-methoxyquinazoline The amine used was ethylamine.

Yield: 47 mg, 24%; $^1$H NMR Spectrum: (CDCl$_3$) 1.17 (t, 3H), 1.98 (m, 2H), 2.09 (m, 2H), 2.45 (m, 2H), 2.87 (m, 2H), 3.05 (s, 2H), 3.33 (m, 2H), 4.02 (s, 3H), 4.49 (m, 1H), 7.16 (m, 4H), 7.30 (s, 1H), 7.33 (s br, 1H), 8.48 (m, 1H), 8.71 (s, 1H); Mass spectrum: MH$^+$ 488.

EXAMPLE 7

4-(3-chloro-2-fluoroanilino)-7-methoxy-6-{[1-(N-[2-(pyrrolidin-1-yl)ethyl]carbamoylmethyl)piperidin-4-yl]oxy}quinazoline The amine used was 1-(2-aminoethyl)pyrrolidine.

Yield: 53 mg, 24%; $^1$H NMR Spectrum: (CDCl$_3$) 1.80 (m, 4H), 1.98 (m, 2H), 2.07 (m, 2H), 2.45 (m, 2H), 2.53 (m, 4H), 2.62 (t, 2H), 2.87 (m, 2H), 3.07 (s, 2H), 3.40 (m, 2H), 4.02 (s, 3H), 4.48 (m, 1H), 7.16 (m, 3H), 7.31 (m, 2H), 7.55 (s br 1H), 8.50 (m, 1H), 8.71 (s, 1H); Mass spectrum: MH$^+$ 557.

EXAMPLE 8

4-(3-chloro-2-fluoroanilino)-7-methoxy-6-{[1-(N-(2-methyoxyethyl)carbamoylmethyl)piperidin-4-yl]oxy}quinazoline The amine used was 2-methoxyethylamine.

Yield: 57 mg, 28%; $^1$H NMR Spectrum: (CDCl$_3$) 1.98 (m, 2H), 2.09 (m, 2H), 2.45 (m, 2H), 2.87 (m, 2H), 3.07 (s, 2H), 3.38 (s, 3H), 3.48 (s, 4H), 4.02 (s, 3H), 4.49 (m, 1H), 7.16 (m, 3H), 7.31 (m, 2H), 7.48 (s br, 1H), 8.49 (m, 1H), 8.71 (s, 1H); Mass spectrum: MH$^+$ 518.

EXAMPLE 9

4-(3-chloro-2-fluoroanilino)-6-{[1-(N-(2-dimethylaminoethyl)carbamoylmethyl)piperidin-4-yl]oxy}-7-methoxyquinazoline The amine used was N,N-dimethylethylenediamine.

Yield 79 mg, 37%; $^1$H NMR Spectrum: (CDCl$_3$) 1.98 (m, 2H), 2.10 (m, 2H), 2.26 (s, 6H), 2.43 (m, 4H), 2.88 (m, 2H), 3.07 (s, 2H), 3.37 (m, 2H), 3.48 (s br, 1H), 4.03 (s, 3H), 4.49

(m, 1H), 7.16 (m, 3H), 7.31 (m, 2H), 7.51 (s br, 1H), 8.49 (m, 1H), 8.71 (s, 1H); Mass spectrum: MH+ 531.

EXAMPLE 10

4-(3-chloro-2-fluoroanilino)-7-methoxy-6-({1-[2-(4-methylpiperazin-1-yl)-2-oxoethyl]piperidin-4-yl}oxy)quinazoline The amine used was N-methylpiperazine.
Yield: 64 mg, 30%; 1H NMR Spectrum: (CDCl3) 1.96 (m, 2H), 2.11 (m, 2H), 2.32 (s, 3H), 2.40 (m, 6H), 2.87 (m, 2H), 3.24 (s, 2H), 3.65 (m, 4H), 4.02 (s, 3H), 4.47 (m, 1H), 7.16 (m, 3H), 7.30 (m, 1H), 7.33 (s br, 1H), 8.48 (m, 1H), 8.70 (s, 1H); Mass spectrum: MH+ 543.

EXAMPLE 11

4-(3-chloro-2-fluoroanilino)-7-methoxy-6-({1-[2-(piperazin-1-yl)-2-oxoethyl]piperidin-4-yl}oxy)quinazoline The procedure according to Examples 6 to 10 was used except that 1-tert-butoxycarbonylpiperazine was used as the amine and that after the aqueous work-up, the residue was stirred for 90 minutes in a 1:1 mixture of dichloromethane-trifluoroacetic acid (3 ml) and then purified by HPLC.
Yield: (150 mg from a 0.56 mmol scale, 51%); 1H NMR Spectrum: (CDCl3) 1.96 (m, 2H), 2.11 (m, 2H), 2.41 (m, 2H), 2.87 (m, 6H), 3.23 (s, 2H), 3.59 (m, 4H), 4.01 (s, 3H), 4.46 (m, 1H), 7.16 (m, 3H), 7.29 (s, 1H), 7.41 (s br, 1H), 8.45 (m, 1H), 8.70 (s, 1H); Mass spectrum: MH+ 529.
The [4-({4-(3-chloro-2-fluoroanilino)-7-methoxyquinazolin-6-yl}oxy)piperidin-1-yl]acetic acid dihydrochloride salt used as starting material was made as follows:
Tert-butyl chloroacetate (1.43 ml, 10 mmol) was added dropwise to a mixture of 4-(3-chloro-2-fluoroanilino)-7-methoxy-6-[(piperidin-4-yl)oxy]quinazoline (4.02 g, 10 mmol), potassium iodide (1.66 g, 10 mmol) and potassium carbonate (1.66 g, 12 mmol) in dimethylacetamide (50 ml). The mixture was heated at 70° C. for one hour. After evaporation of the solvents under vacuum, the residue was triturated in water. The resulting solid was filtered, washed with water and purified by chromatography on silica gel (eluant: 2% 7N methanolic ammonia in dichloromethane) to give tert-butyl [4-({4-(3-chloro-2-fluoroanilino)-7-methoxyquinazolin-6-yl}oxy)piperidin-1-yl]acetate as a white solid (3.0 g, 60%).
NMR Spectrum: (CDCl3) 1.48 (s, 9H), 2.01 (m, 2H), 2.10 (m, 2H), 2.56 (m, 2H), 2.89 (m, 2H), 3.19 (s, 2H), 4.01 (s, 3H), 4.49 (m, 1H), 7.16 (m, 3H), 7.29 (m, 2H), 8.48 (m, 1H), 8.70 (s, 1H); Mass spectrum: MH+ 517.
A suspension of ten-butyl[4-({4-(3-chloro-2-fluoroanilino)-7-methoxyquinazolin-6-yl}oxy)piperidin-1-yl]acetate (3.0 g, 5.8 mmol) in a solution of 4N hydrogen chloride in dioxane (40 ml) was stirred at room temperature for 3 hours. The solvents were evaporated under high vacuum. The residue was triturated in ether, filtered and washed with ether to give [4-({4-(3-chloro-2-fluoroanilino)-7-methoxyquinazolin-6-yl}oxy)piperidin-1-yl]acetic acid as the dihydrochloride salt (3.1 g, 100%). Mass spectrum: MH+ 461.

EXAMPLE 12

4-(3-chloro-2,4-difluoroanilino)-7-methoxy-6-({1-[2-(4-methylpiperazin-1-yl)-2-oxoethyl]piperidin-4-yl}oxy)quinazoline

[4-({4-(3-chloro-2,4-difluoroanilino)-7-methoxyquinazolin-6-yl}oxy)piperidin-1-yl]acetic acid dihydrochloride salt and N-methylpiperazine were converted to the title compound (126 mg, 56%) using the procedure according to Examples 6 to 10.
1H NMR Spectrum: (CDCl3) 1.94 (m, 2H), 2.09 (m, 2H), 2.31 (s, 3H), 2.40 (m, 6H), 2.84 (m, 2H), 3.23 (s, 2H), 3.65 (m, 4H), 4.01 (s, 3H), 4.45 (m, 1H), 7.06 (m, 1H), 7.22 (s, 1H), 7.29 (m, 1H), 7.36 (s br, 1H), 8.28 (m, 1H), 8.65 (s, 1H); Mass spectrum: MH+ 561
The [4-({4-(3-chloro-2,4-difluoroanilino)-7-methoxyquinazolin-6-yl}oxy)piperidin-1-yl]acetic acid dihydrochloride salt used as starting material was made from 4-(3-chloro-2,4-difluoroanilino)-7-methoxy-6-[(piperidin-4-yl)oxy]quinazoline using the same procedure as described in Example 11:
tert-Butyl[4-({4-(3-chloro-2,4-difluoroanilino)-7-methoxyquinazolin-6-yl}oxy)piperidin-1-yl]acetate (2.56 g, 67%): Mass spectrum: MH+ 535.
[4-({4-(3-chloro-2,4-difluoroanilino)-7-methoxyquinazolin-6-yl}oxy)piperidin-1-yl]acetic acid (dihydrochloride salt, 2.45 g, 93%): Mass spectrum: MH+ 479.

EXAMPLE 13

Pharmaceutical Compositions
The following illustrates a representative pharmaceutical dosage forms of the invention as defined herein (the active ingredient being termed "Compound X"), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Injection I | (50 mg/ml) |
|---|---|
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100%. | |

The above formulations may be obtained by conventional procedures well known in the pharmaceutical art. For example the tablet may be prepared by blending the components together and compressing the mixture into a tablet.

The invention claimed is:
1. A compound chosen from 4-(3-chloro-2-fluoroanilino)-7-methoxy-6-{[1-(N-methylcarbamoylmethyl)piperidin-4-yl]-oxy}quinazoline and its pharmaceutically acceptable salts.
2. A pharmaceutical composition comprising at least one compound chosen from 4-(3-chloro-2-fluoroanilino)-7-methoxy-6-{[1-(N-methylcarbamoylmethyl)piperidin-4-yl]-oxy}quinazoline and its pharmaceutically acceptable salts in association with a pharmaceutically-acceptable diluent or carrier.
3. A compound chosen from 4-(3-chloro-2-fluoroanilino)-7-methoxy-6-{[1-(N-methylcarbamoylmethyl)piperidin-4-yl]-oxy}quinazoline.
4. A pharmaceutical composition comprising 4-(3-chloro-2-fluoroanilino)-7-methoxy-6-{[1-(N-methylcarbamoylmethyl)piperidin-4-yl]oxy}-quinazoline in association with a pharmaceutically-acceptable diluent or carrier.

5. A pharmaceutically acceptable salt of 4-(3-chloro-2-fluoroanilino)-7-methoxy-6-{[1-(N-methylcarbamoylmethyl)piperidin-4-yl]-oxy}quinazoline.

6. A pharmaceutical composition comprising a pharmaceutically acceptable salt of 4-(3-chloro-2-fluoroanilino)-7-methoxy-6-{[1-(N-methylcarbamoylmethyl)piperidin-4-yl]-oxy}quinazoline in association with a pharmaceutically-acceptable diluent or carrier.

* * * * *